(12) United States Patent
Dominowski et al.

(10) Patent No.: US 7,736,658 B2
(45) Date of Patent: Jun. 15, 2010

(54) CANINE COMBINATION VACCINES

(75) Inventors: Paul J. Dominowski, Hickory Corners, MI (US); Joseph C. Frantz, Denton, NE (US); Richard L. Krebs, Ashland, NE (US); Shelly L. Shields, Plainwell, MI (US); Robert Greg Sorensen, Lincoln, NE (US)

(73) Assignee: Pfizer Inc., New York, NY (US)

( * ) Notice: Subject to any disclaimer, the term of this patent is extended or adjusted under 35 U.S.C. 154(b) by 9 days.

(21) Appl. No.: 11/942,843

(22) Filed: Nov. 20, 2007

(65) Prior Publication Data

US 2008/0226670 A1 Sep. 18, 2008

Related U.S. Application Data

(62) Division of application No. 10/767,809, filed on Jan. 29, 2004, now abandoned.

(60) Provisional application No. 60/443,418, filed on Jan. 29, 2003.

(51) Int. Cl.
*A61K 39/295* (2006.01)
*A61P 31/12* (2006.01)
*A61P 31/04* (2006.01)

(52) U.S. Cl. .............. 424/201.1; 424/184.1; 424/185.1; 424/190.1; 424/203.1

(58) Field of Classification Search ........................ None
See application file for complete search history.

(56) References Cited

U.S. PATENT DOCUMENTS

| | | | | |
|---|---|---|---|---|
| 3,950,512 | A | * 4/1976 | Emery et al. | ............. 424/201.1 |
| 4,567,042 | A | 1/1986 | Acree et al. | |
| 4,567,043 | A | 1/1986 | Acree et al. | |
| 4,810,494 | A | * 3/1989 | Welsh | ...................... 424/201.1 |
| 4,824,785 | A | 4/1989 | Acree et al. | |

FOREIGN PATENT DOCUMENTS

| | | | |
|---|---|---|---|
| EP | 465204 | A2 * | 1/1992 |
| EP | 0 535 740 | | 4/1993 |
| EP | 1016416 | A2 * | 7/2000 |
| EP | 1 023 904 | | 8/2000 |
| GB | 2048669 | A * | 12/1980 |
| JP | 6228010 | | 8/1994 |
| WO | 90/03184 | | 4/1990 |
| WO | 92/17587 | | 10/1992 |
| WO | 96/33739 | | 10/1996 |

OTHER PUBLICATIONS

Shahin et al., "Characterization of the Protective Capacity and Immunogenicity of the 69-kD Outer Membrane Protein of *Bordetella pertussis*", J. Exp. Med., 171:63-73, 1990.
Novotny et al., "Biologic and Protective Properties of the 69-kDa Outer Membrane Protein of *Bordetella pertussis*: A Novel Formation for an Acellular Pertussis Vaccine", J. Infect. Dis., 164:114-122, 1991.
He et al., "Protective Role of Immunoglobulin G Antibodies to Filamentous Hemagglutinin and Pertactin of *Bordetelle pertussis* in *Bordetella parapertussis* Infection", Eur. J. Clin. Microbiol. Infect. Dis., 15(10):793-798, 1996.
Kobisch et al., "Identification of a 68-Kilodalton Outer Membrane Protein as the Major Protective Antigen of *Bordetella bronchiseptica* by Using Specific-Pathogen-Free Piglets", Infect. Immun., 58(2):352-357, 1990.
Montaraz, et al., Identification of a 68-Kilodalton Protective Protein Antigen from *Bordetella bronchiseptica*, Infect. Immun., 47(3):744-751, 1985.
Mackintosh et al., "The use of a hardjo-pomona vaccine to prevent leptospiruria in cattle exposed to natural challenge with *Leptospira interrogans* serovar hardjo", New Zealand Veterinary Journal, 28(9):174-177, 1980.
Bolin et al., "Effect of vaccination with a pentavalent leptospiral vaccine on *Leptospira interrogans* serovar hardjo type hardjo-bovis infection of pregnant cattle", Am. J. Vet. Res., 50(1):161-165, 1989.
Novotny et al., "Evaluation of *Bordetella bronchiseptica* Vaccines in Specific-Pathogen-Free Piglets with Bacterial Cell Surface Antigens in Enzyme-Linked Immunosorbent Assay", Infect. Immun., 50(1):190-198, 1985.
Novotny et al., "Adenylate Cyclase Activity of a 68,000-Molecular-Weight Protein Isolated from the Outer Membrane of *Bordetella bronchiseptica*", Infect. Immun., 50(1):199-206, 1985.
PCT International Search Report, PCT/IB2004/00146.

* cited by examiner

*Primary Examiner*—Robert A Zeman
(74) *Attorney, Agent, or Firm*—Timothy J. Gumbleton

(57) ABSTRACT

This invention relates to vaccines and methods for protecting dogs against disease caused by *Bordetella bronchiseptica*. This invention also relates to combination vaccines and methods for protecting dogs against disease or disorder caused by canine pathogens, for example, infectious tracheobronchitis caused by *Bordetella bronchiseptica*, canine distemper caused by canine distemper (CD) virus, infectious canine hepatitis (ICH) caused by canine adenovirus type 1 (CAV-1), respiratory disease caused by canine adenovirus type 2 (CAV-2), canine parainfluenza caused by canine parainfluenza (CPI) virus, enteritis caused by canine coronavirus (CCV) and canine parvovirus (CPV), and leptospirosis caused by *Leptospira Bratislava, Leptospira canicola, Leptospira grippotyphosa, Leptospira icterohaemorrhagiae* or *Leptospira pomona*. The vaccines of the present invention include a *Bordetella bronchiseptica* p68 antigen.

11 Claims, 5 Drawing Sheets

Figure 1: Summary of Geometric Mean of P68 ELISA Endpoint Titers in Unvaccinated and p68 Bordetella (15 μg/dose) Vaccinated Dogs Aerosol Challenge with Bordetella Bronchiseptica
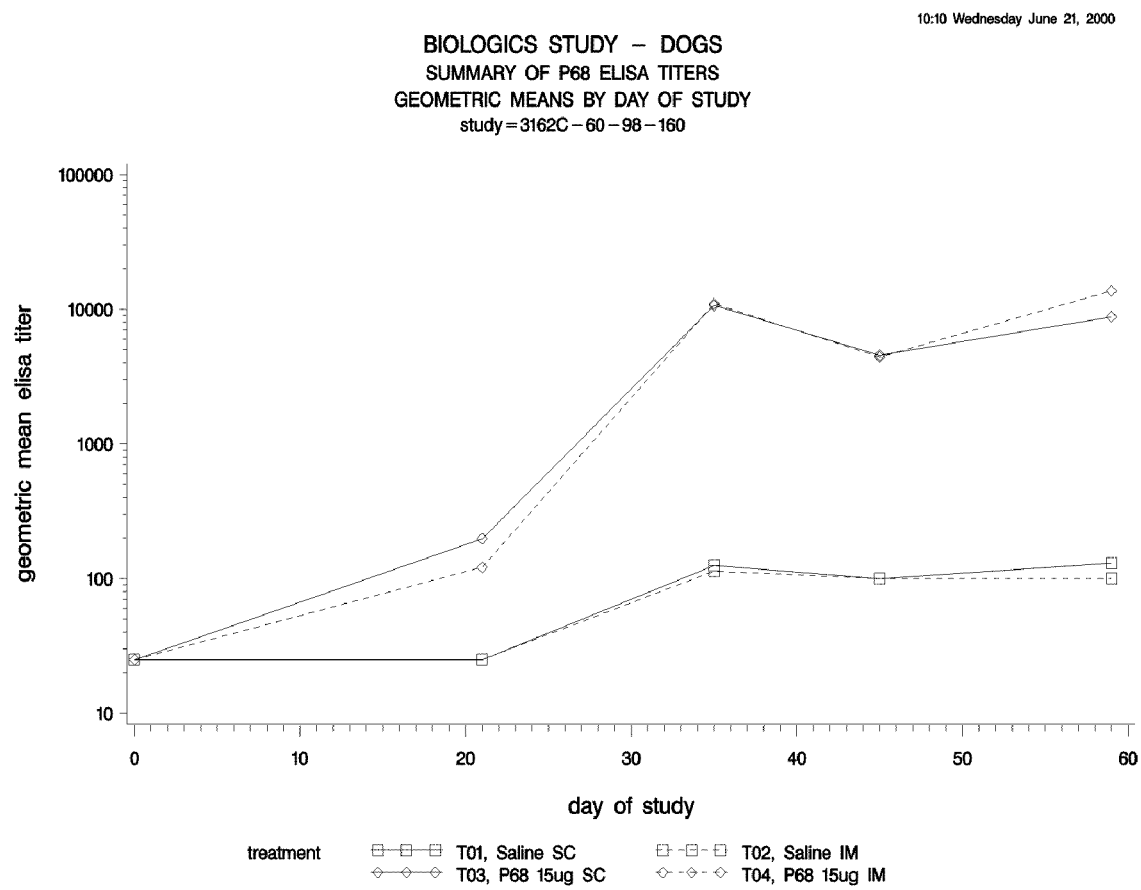

Figure 2. Summary of Serum Amyloid A titers in Dogs Following Aerosol Challenge with *Bordetella bronchiseptica*

BIOLOGICS STUDY – DOGS
REPEATED MEASURES ANALYSIS OF SERUM AMYLOID A (SAA) TITERS
GEOMETRIC MEANS BY DAY OF STUDY
study=3162C-60-98-160

10:10 Wednesday June 21, 2000 treatment
□—□—□ T01, Saline SC          □--□--□ T02, Saline IM
◇—◇—◇ T03, P68 16ug SC        ◇--◇--◇ T04, P68 15ug IM

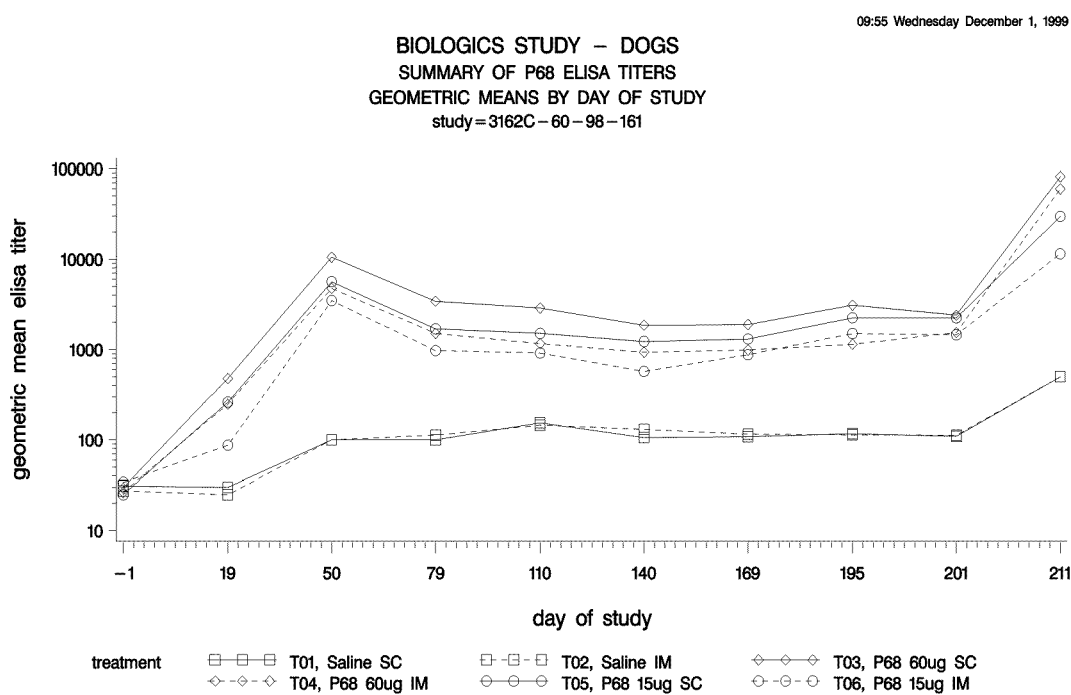
Figure 3 Summary of Geometric Mean of P68 ELISA Endpoint Titers in Unvaccinated and p68 Bordetella Vaccinated Dogs following Vaccination and Aerosol Challenge with Bordetella Bronchiseptica
Day 79 corresponds to combined data from day 79 and 81, day 110 corresponds to 110 and 111, day 169 corresponds to 169 and 170.

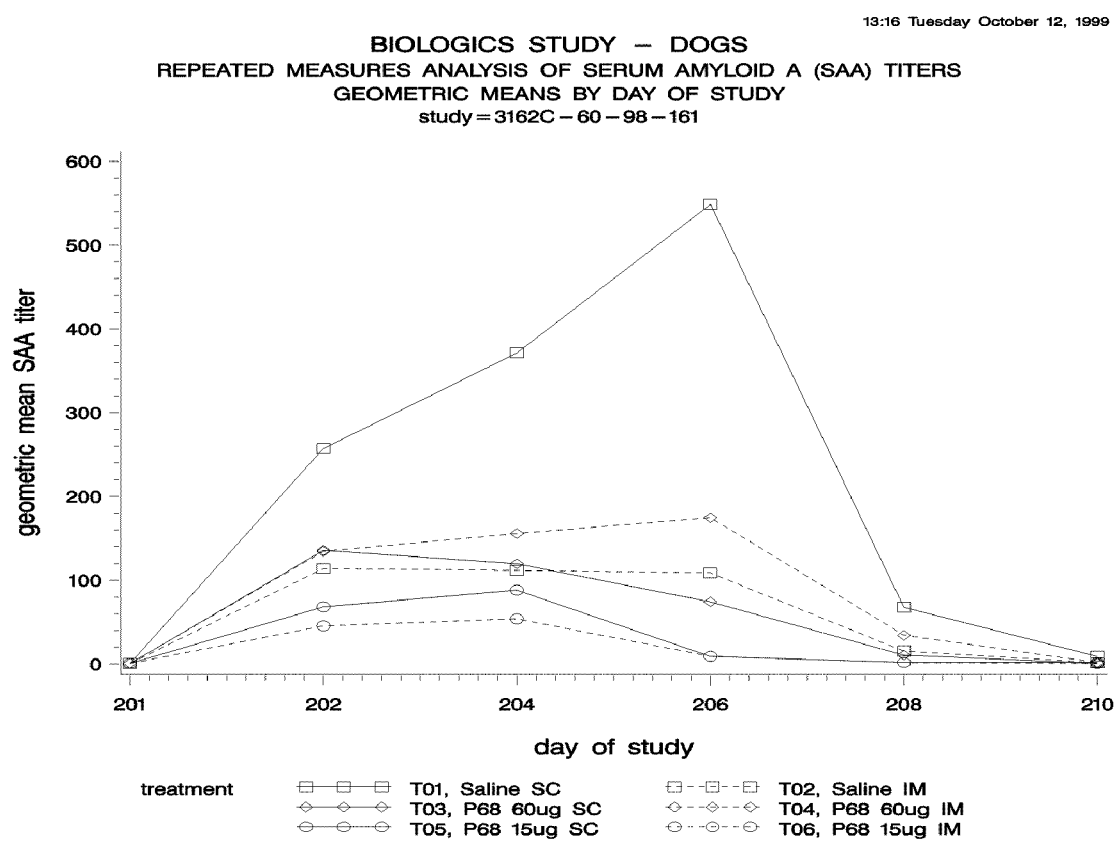
Figure 4. Summary of Serum Amyloid A titers in Dogs Following Aerosol Challenge with *Bordetella bronchiseptica*

CANINE COMBINATION VACCINES

CROSS REFERENCE TO RELATED APPLICATIONS

This application is a divisional of U.S. patent application Ser. No. 10/767,809, filed Jan. 29, 2004, now abandoned, which claims the benefit of U.S. Provisional Patent Application Ser. No. 60/443,418, filed Jan. 29, 2003. The disclosures of both applications are incorporated herein by reference in their entirety.

FIELD OF THE INVENTION

This invention relates to vaccines containing a *Bordetella bronchiseptica* p68 antigen and the use thereof for protecting dogs against infectious tracheobronchitis ("kennel cough") caused by *Bordetella bronchiseptica*. This invention also relates to combination vaccines containing a *Bordetella bronchiseptica* p68 antigen and one or more antigens of another canine pathogen such as canine distemper (CD) virus, canine adenovirus type 2 (CAV-2), canine parainfluenza (CPI) virus, canine coronavirus (CCV), canine parvovirus (CPV), *Leptospira bratislava, Leptospira canicola, Leptospira grippotyphosa, Leptospira icterohaemorrhagiae* or *Leptospira pomona*. Methods for protecting dogs against diseases caused by canine pathogens using combination vaccines are also provided.

BACKGROUND OF THE INVENTION

The present commercially available canine *Bordetella bronchiseptica* vaccine product is composed of an inactivated, nonadjuvanted *Bordetella bronchiseptica* whole cell bacterin. Such whole cell bacterin can lead to cell protein related post-vaccination reactions. The p68 protein of *B. bronchiseptica* is antigenically similar to the Outer Membrane Protein (OMP) of *B. pertussis* and the OMP of *B. parapertussis* (Shahin et al., "Characterization of the Protective Capacity and Immunogenicity of the 69-kD Outer Membrane Protein of *Bordetella pertussis*", *J. Exp. Med.*, 171: 63-73, 1990). A protective role of this OMP has been demonstrated for mice (Shahin et al., supra; Novotny et al., "Biologic and Protective Properties of the 69-kD Outer Membrane Protein of *Bordetella pertussis*: A Novel Formulation for a Acellular Pertussis Vaccine", *J. Infect. Dis.* 164:114-22, 1991), humans (He et al., "Protective Role of Immunoglobulin G Antibodies to Filamentous Hemagglutinin and Pertactin of *Bordetella pertussis* in *Bordetella* parapertussis Infection", *Eur. J. Clin Microbiol Infect Dis.* 10:793-798, 1996) and swine (Kobisch et al., "Identification of a 68-Kilodalton Outer Membrane Protein as the Major Protective Antigen of *Bordetella bronchiseptica* by Using Specific-Pathogen-Free Piglets", *Infect. Immun.* 58(2):352-357, 1990).

Prior to the present invention, there had been no showing that a *Bordetella bronchiseptica* p68 antigen can be a safe and effective vaccine in dogs. Therefore, there is a need to develop a *Bordetella bronchiseptica* vaccine containing a p68 antigen that is suitable for canine use. It would be even more advantageous if such a *Bordetella bronchiseptica* p68 vaccine is safe for administration to puppies and provides a long-term protection.

CD is a universal, high-mortality viral disease with variable manifestations. Approximately 50% of nonvaccinated, nonimmune dogs infected with CD virus develop clinical signs, and approximately 90% of those dogs die.

Infectious canine hepatitis or ICH, caused by canine adenovirus type 1 (CAV-1), is a universal, sometimes fatal, viral disease of dogs characterized by hepatic and generalized endothelial lesions. CAV-2 causes respiratory disease, which, in severe cases, may include pneumonia and bronchopneumonia.

CPI is a common viral upper respiratory disease. Uncomplicated CPI may be mild or subclinical, with signs becoming more severe if concurrent infection with other respiratory pathogens exists.

CPV infection results in enteric disease characterized by sudden onset of vomiting and diarrhea, often hemorrhagic. Leukopenia commonly accompanies clinical signs. Susceptible dogs of any age can be affected, but mortality is greatest in puppies. In puppies 4-12 weeks of age CPV may occasionally cause myocarditis that can result in acute heart failure after a brief and inconspicuous illness. Following infection many dogs are refractory to the disease for a year or more. Similarly, seropositive bitches may transfer to their puppies CPV antibodies which can interfere with active immunization of the puppies through 16 weeks of age.

CCV also causes enteric disease in susceptible dogs of all ages worldwide. Highly contagious, the virus is transmitted primarily through direct contact with infectious feces, and may cause clinical enteritis within 1-4 days after exposure. Severity of disease may be exacerbated by concurrent infection with other agents. Primary signs of CCV infection include anorexia, vomiting, and diarrhea. Frequency of vomiting usually diminishes within a day or 2 after onset of diarrhea, but diarrhea may linger through the course of infection, and stools occasionally may contain streaks of blood. With CCV infection most dogs remain afebrile and leukopenia is not observed in uncomplicated cases.

Leptospirosis occurs in dogs of all ages, with a wide range of clinical signs and chronic nephritis generally following acute infection. Infection with *L. canicola* and *L. icterohaemorrhagiae* cannot be differentiated clinically.

Prior to the present invention, there have been no effective combination vaccines that protect dogs against *Bordetella bronchiseptica* and one or more of other canine pathogens such as CD virus, CAV-2, CPI virus, CPV, CCV, and a *Leptospira* species such as *L. bratislava, L. canicola, L. grippotyphosa, L. icterohaemorrhagiae* and *L. pomona*. A problem in developing combination vaccines involves efficacy interference, namely a failure of one or more antigens in a combination composition to maintain or achieve efficacy because of the presence of the other antigens in the composition. This is believed to be a result of interference with an antigen in the composition administered to a host, e.g., a dog, in the immunological, antigenic, antibody or protective response such antigen induced in the host because of the other antigens present in the composition. However, for other hosts, such as cats, combination vaccines are known. It is believed that efficacy interference in dogs is due to some peculiarity of the canine biological system, or due to the reaction of the antigens with the canine biological system.

There is a need, therefore, to develop a combination vaccine suitable for administration to dogs against *Bordetella bronchiseptica* and one or more other canine pathogens, which does not exhibit efficacy interference in canines. It would be even more advantageous if such a combination vaccine is safe for administration to puppies and provides long-term protection.

SUMMARY OF THE INVENTION

The present invention provides vaccines and methods for protecting dogs against diseases caused by canine pathogens.

In one embodiment, the present invention provides p68 vaccines suitable for administration to dogs and capable of protecting dogs against disease caused by *Bordetella bronchiseptica*. Such vaccines of the present invention include a Bordetella bronchiseptica p68 antigen and a veterinary-acceptable carrier such as an adjuvant.

In another embodiment, the present invention provides methods of protecting dogs against disease caused by *Bordetella bronchiseptica* by administering to a dog a vaccine which includes a *Bordetella bronchiseptica* p68 antigen and a veterinary-acceptable carrier such as an adjuvant.

In still another embodiment, the present invention provides combination vaccines suitable for administration to dogs. The combination vaccines of the present invention include a *Bordetella bronchiseptica* p68 antigen in combination with one or more of another antigen from other canine pathogens, capable of inducing a protective immune response in dogs against disease caused by such other pathogen(s). Such other pathogens can be selected from canine distemper (CD) virus, canine adenovirus type 2 (CAV-2), canine parainfluenza (CPI) virus, canine parvovirus (CPV), canine coronavirus (CCV), canine herpesvirus, rabies virus, *Leptospira bratislava, Leptospira canicola, Leptospira grippotyphosa, Leptospira icterohaemorrhagiae, Leptospira pomona, Leptospira hardjobovis, Porphyromonas* spp., *Bacteriodes* spp., *Leishmania* spp., *Borrelia* spp., *Ehrlichia* spp., *Mycoplasma* spp. and *Microsporum canis*.

A preferred combination vaccine of the present invention includes therapeutically effective amounts of attenuated strains of canine distemper (CD) virus, canine adenovirus type 2 (CAV-2), canine parainfluenza (CPI) virus and canine parvovirus (CPV); an inactivated preparation of a strain of canine coronavirus (CCV); and a *Bordetella bronchiseptica* p68 antigen.

Another preferred combination vaccine of the present invention includes therapeutically effective amounts of attenuated strains of canine distemper (CD) virus, canine adenovirus type 2 (CAV-2), canine parainfluenza (CPI) virus and canine parvovirus (CPV); an inactivated preparation of a strain of canine coronavirus (CCV); a *Bordetella bronchiseptica* p68 protein, and an inactivated cell preparation of therapeutically effective amounts of five *Leptospira* serovars (*Leptospira bratislava, Leptospira canicola, Leptospira grippotyphosa, Leptospira icterohaemorrhagiae* and *Leptospira pomona*).

Still another preferred combination vaccine of the present invention includes therapeutically effective amounts of attenuated strains of CD virus, CAV-2, CPI virus, a CPV strain; and a *Bordetella bronchiseptica* p68 antigen.

Another preferred combination vaccine of the present invention includes therapeutically effective amounts of attenuated strains of CD virus, CAV-2, CPI virus, a CPV strain; a *Bordetella bronchiseptica* p68 antigen; and an inactivated cell preparation of therapeutically effective amounts of *Leptospira canicola* and *Leptospira icterohaemorrhagiae*.

Still another preferred combination vaccine of the present invention includes therapeutically effective amounts attenuated strains of CD virus, CAV-2, CPI virus, a CPV strain, a *Bordetella bronchiseptica* p68 antigen and an inactivated cell preparation of therapeutically effective amounts of five *Leptospira* serovars (*Leptospira bratislava, Leptospira canicola, Leptospira grippotyphosa, Leptospira icterohaemorrhagiae* and *Leptospira pomona*).

Another preferred combination vaccine includes therapeutically effective amounts of a *Bordetella bronchiseptica* p68 antigen and an attenuated CPI virus.

Still another preferred combination vaccine includes therapeutically effective amounts of a *Bordetella bronchiseptica* p68 antigen, an attenuated CPI virus and an inactivated cell preparation of therapeutically effective amounts of *Leptospira canicola* and *Leptospira icterohaemorrhagiae*.

The present invention also provides methods of protecting dogs against disease caused by a canine pathogen by administering to a dog a combination vaccine of the present invention.

BRIEF DESCRIPTION OF THE DRAWINGS

FIG. 1. Summary of the geometric mean of p68 ELISA endpoint titers in unvaccinated and *Bordetella* p68 (15 μg/dose) vaccinated dogs-aerosol challenge with *Bordetella bronchiseptica*.

FIG. 2. Summary of Serum Amyloid A titers in dogs following aerosol challenge with *Bordetella bronchiseptica*.

FIG. 3. Summary of the geometric mean of p68 ELISA endpoint titers in unvaccinated and *Bordetella* p68 vaccinated dogs following vaccination and aerosol challenge with *Bordetella bronchiseptica*.

FIG. 4. Summary of Serum Amyloid A titers in dogs following aerosol challenge with *Bordetella bronchiseptica*.

DETAILED DESCRIPTION OF THE INVENTION

Figure 5:
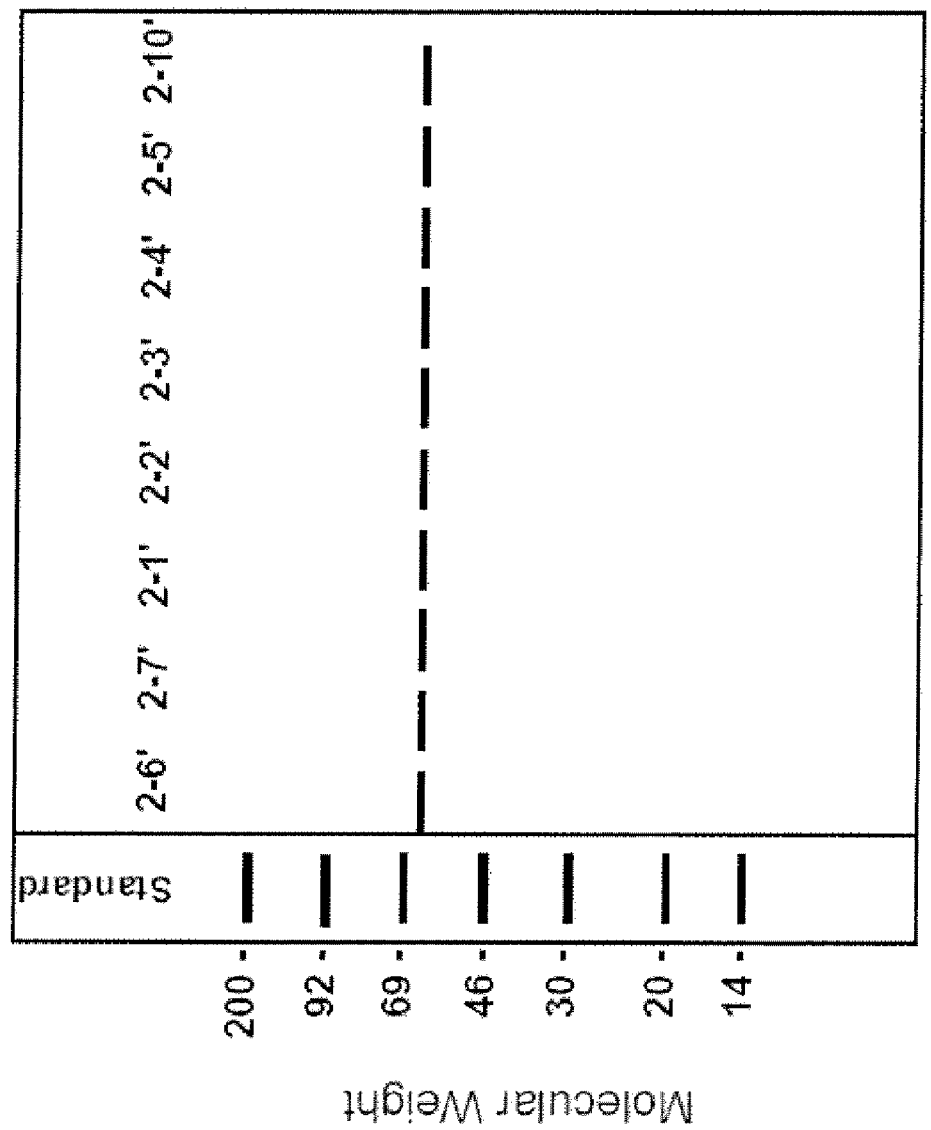
FIG. 5. Western blot showing reactivity of p68 monoclonal antibody Bord 2-7 to p68 whole cell lysate.

In one embodiment, the present invention provides monovalent vaccines suitable for administration to dogs which are capable of protecting dogs against disease caused by *Bordetella bronchiseptica*. The monovalent vaccines of the present invention include a recombinantly produced *Bordetella bronchiseptica* p68 antigen and a veterinary-acceptable carrier such as an adjuvant.

In another embodiment, the present invention provides methods of protecting dogs against disease caused by *Bordetella bronchiseptica* by administering to a dog a monovalent vaccine which includes a recombinantly produced *Bordetella bronchiseptica* p68 antigen and a veterinary-acceptable carrier such as an adjuvant.

In still another embodiment, the present invention provides combination vaccines suitable for administration to dogs. The combination vaccines of the present invention include a recombinantly produced *Bordetella bronchiseptica* p68 antigen in combination with one or more of another antigen capable of inducing a protective immune response in dogs against disease caused by such other antigen.

A preferred combination vaccine of the present invention includes attenuated strains of canine distemper (CD) virus, canine adenovirus type 2 (CAV-2), canine parainfluenza (CPI) virus and canine parvovirus (CPV); an inactivated preparation of a strain of canine coronavirus (CCV); and a *Bordetella bronchiseptica* p68 protein.

Another preferred combination vaccine of the present invention includes attenuated strains of canine distemper (CD) virus, canine adenovirus type 2 (CAV-2), canine parainfluenza (CPI) virus and canine parvovirus (CPV); an inactivated preparation of a strain of canine coronavirus (CCV); a *Bordetella bronchiseptica* p68 protein, and a preparation of five *Leptospira* serovars (*Leptospira Bratislava, Leptospira canicola, Leptospira grippotyphosa, Leptospira icterohaemorrhagiae* and *Leptospira pomona*).

Still another preferred combination vaccine of the present invention includes attenuated strains of CD virus, CAV-2, CPI virus, a CPV strain; and a *Bordetella bronchiseptica* p68 protein.

Another preferred combination vaccine of the present invention includes attenuated strains of CD virus, CAV-2, CPI virus, a CPV strain; a *Bordetella bronchiseptica* p68 protein; and a preparation of *Leptospira canicola* and *Leptospira icterohaemorrhagiae*.

Still another preferred combination vaccine of the present invention includes attenuated strains of CD virus, CAV-2, CPI virus, a CPV strain and a preparation of five *Leptospira* serovars (*Leptospira bratislava, Leptospira canicola, Leptospira grippotyphosa, Leptospira icterohaemorrhagiae* and *Leptospira pomona*).

The present invention also provides methods of protecting dogs against disease caused by a canine pathogen by administering to a dog a combination vaccine of the present invention.

For clarity of disclosure, and not by way of limitation, the detailed description of the invention is divided into the following subsections which describe or illustrate certain features, embodiments or applications of the invention.

DEFINITIONS AND ABBREVIATIONS

The term "protecting a dog against a disease caused by a canine pathogen" as used herein means reducing or eliminating the risk of infection by the pathogen, ameliorating or alleviating the symptoms of an infection, or accelerating the recovery from an infection. Protection is achieved if there is a reduction in viral or bacterial load, a reduction in viral or bacterial shedding, a decrease in incidence or duration of infections, reduced acute phase serum protein levels, reduced rectal temperatures, and/or increase in food uptake and/or growth, for example.

The term "p68 antigen" refers to a protein with a molecular weight of 68 kDa as determined by SDS polyacrylamide gel electrophoresis, is recognized by the p68-specific monoclonal antibody Bord 2-7 (ATCC#), and has an amino acid sequence as set forth in SEQ ID NO: 1 or an amino acid sequence that is substantially identical to SEQ ID NO: 1.

By "substantially identical" is meant a degree of sequence identity of at least about 90%, preferably at least about 95%, or more preferably, at least about 98%.

The term "monovalent vaccine" as used herein refers to a vaccine having one principal antigenic component. For example, a p68 monovalent vaccine includes a *Bordetella bronchiseptica* p68 antigen as the principal antigenic component of the vaccine and is capable of protecting the animal to which the vaccine is administered against diseases caused by *Bordetella bronchiseptica*.

The term "combination vaccine" is meant a bivalent or multivalent combination of antigens which are capable of inducing a protective immune response in dogs. The protective effects of a combination vaccine against a pathogen or pathogens are normally achieved by inducing in the animal subject an immune response, either a cell-mediated or a humoral immune response or a combination of both.

By "immunogenic" is meant the capacity of a composition to provoke an immune response in dogs against a particular pathogen. The immune response can be a cellular immune response mediated primarily by cytotoxic T-cells and cytokine-producing T-cells, or a humoral immune response mediated primarily by helper T-cells, which in turn activates B-cells leading to antibody production.

The term "therapeutically effective amount" or "effective amount" refers to an amount of a monovalent or combination vaccine sufficient to elicit a protective immune response in the dog to which it is administered. The immune response may comprise, without limitation, induction of cellular and/or humoral immunity. The amount of a vaccine that is therapeutically effective may vary depending on the particular antigen used in the vaccine, the age and condition of the dog, and/or the degree of infection, and can be determined by a veterinary physician.

p68 Vaccines

The present invention has demonstrated for the first time that a vaccine composition containing a *Bordetella bronchiseptica* p68 antigen effectively protected dogs against disease caused by *Bordetella bronchiseptica*. The vaccine composition of the present invention does not cause significant post-vaccination reactions, is safe for administration to puppies, and induces protective immunity in dogs that lasts for an extended period of time.

Accordingly, one embodiment of the present invention is directed to a vaccine composition containing a *Bordetella bronchiseptica* p68 antigen (or "a p68 vaccine"), that is suitable for administration to dogs and is capable of protecting dogs against disease caused by *Bordetella bronchiseptica*, e.g., infectious tracheobronchitis ("kennel cough").

For the purpose of the present invention, the term "p68 antigen" refers to a protein with a molecular weight of 68 kDa as determined by SDS polyacrylamide gel electrophoresis, is recognized by the p68-specific monoclonal antibody Bord 2-7 (ATCC#), and has an amino acid sequence as set forth in SEQ ID NO: 1 or an amino acid sequence that is substantially identical to SEQ ID NO: 1. By "substantially identical" is meant a degree of sequence identity of at least about 90%, preferably at least about 95%, or more preferably, at least about 98%. An example of a p68 antigen having an amino acid sequence substantially identical to SEQ ID NO: 1 is the p68 antigen described in WO 92/17587, which is set forth in SEQ ID NO: 3. The p68 specific monoclonal antibody of the present invention recognizes native p68 proteins, recombinant p68 proteins and p68 proteins on the surface of bacteria, for example.

In accordance with the present invention, p68 antigens suitable for use in the present invention include both native p68 proteins (i.e., naturally occurring p68 proteins purified from *Bordetella bronchiseptica*) and recombinantly produced p68 proteins.

Purification of native p68 from *Bordetella bronchiseptica* is described, e.g., in Montaraz et al., *Infection and Immunity* 47: 744-751 (1985), and is also illustrated in the examples provided hereinbelow. Recombinant production of p68 can be achieved using any one of the molecular cloning and recombinant expression techniques known to those skilled in the art. For example, a nucleic acid molecule encoding p68 can be introduced into an appropriate host cell, such as a bacterium, a yeast cell (e.g., a *Pichia* cell), an insect cell or a mammalian cell (e.g., CHO cell). The p68-encoding nucleic acid molecule can be placed in an operable linkage to a promoter capable of effecting the expression of the p68 antigen in the host cell. p68, which is expressed by the host cell, can be readily purified using routine protein purification techniques.

In a preferred embodiment of the present invention, the nucleotide sequence as set forth in SEQ ID NO: 2 coding for the p68 antigen which has the amino acid sequence of SEQ ID NO: 1, is cloned in an expression vector and placed in an operable linkage to a temperature sensitive promoter. The expression vector is introduced into *Escherichia coli* and the p68 antigen is expressed upon heat induction. The cells are lysed and the inclusion bodies where the p68 antigen accumulates are separated by centrifugation. The recombinant p68 in the inclusion bodies is solubilized using SDS or other solubilization agents known in the art such as urea, guanidine hydrochloride, sodium cholate, taurocholate, and sodium deoxycholate. In accordance with the present invention, a purified native or recombinant p68 protein is combined with a veterinary-acceptable carrier to form a p68 vaccine composition.

The term "a veterinary-acceptable carrier" includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others.

Adjuvants suitable for use in accordance with the present invention include, but are not limited to several adjuvant classes such as; mineral salts, e.g., Alum, aluminum hydroxide, aluminum phosphate and calcium phosphate; surface-active agents and microparticles, e.g., nonionic block polymer surfactants (e.g., cholesterol), virosomes, saponins (e.g., Quil A, QS-21 and GPI-0100), proteosomes, immune stimulating complexes, cochleates, quarterinary amines (dimethyl diocatadecyl ammonium bromide (DDA)), pyridine, vitamin A, vitamin E; bacterial products such as the RIBI adjuvant system (Ribi Inc.), cell wall skeleton of *Mycobactherum phlei* (Detox®), muramyl dipeptides (MDP) and tripeptides (MTP), monophosphoryl lipid A, *Bacillus* Calmete-Guerin, heat labile *E. coli* enterotoxins, cholera toxin, trehalose dimycolate, CpG oligodeoxnucleotides; cytokines and hormones, e.g., interleukins (IL-1, IL-2, IL-6, IL-12, IL-15, IL-18), granulocyte-macrophage colony stimulating factor, dehydroepiandrosterone, 1,25-dihydroxy vitamin $D_3$; polyanions, e.g., dextran; polyacrylics (e.g., polymethylmethacrylate, Carbopol 934P); carriers e.g., tetanus toxid, diptheria toxoid, cholera toxin B subnuit, mutant heat labile enterotoxin of enterotoxigenic *E. coli* (rmLT), heat shock proteins; oil-in-water emulsions e.g., AMPHIGEN® (Hydronics, USA); and water-in-oil emulsions such as, e.g., Freund's complete and incomplete adjuvants.

Preferred adjuvants for use in the vaccines of the present invention include Quil A and cholesterol.

The p68 antigen and the veterinary-acceptable carrier can be combined in any convenient and practical manner to form a vaccine composition, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. Preferably, the vaccine is formulated such that it can be administered to dogs by injection in a dose of about 0.1 to 5 ml, or preferably about 0.5 to 2.5 ml, or even more preferably, in a dose of about 1 ml. When appropriate, the pharmaceutical compositions of the present invention should be made sterile by well-known procedures.

The amount of p68 in the vaccines should be immunizing-effective and is generally in the range of 0.5-1000 µg per dose. Preferably, the amount of p68 is in the range of 1-260 µg per dose. More preferably, the amount of p68 is in the range of 10-100 µg per dose. Even more preferably, the amount of p68 is about 15 to 25 µg per dose.

The amount of adjuvants suitable for use in the vaccines depends upon the nature of the adjuvant used. For example, when Quil A and cholesterol are used as adjuvant, Quil A is generally in an amount of about 1-1000 µg per dose, preferably 30-100 µg per dose, and more preferably, about 50-75 µg per dose; and cholesterol is generally in an amount of about 1-1000 µg per dose, preferably about 30-100 µg per dose, and more preferably, about 50-75 µg per dose.

In another embodiment, the present invention provides methods of protecting dogs against disease caused by *Bordetella bronchiseptica* by administering to a dog a p68 vaccine composition, as described hereinabove. In accordance with the present invention, the p68 vaccine composition provides dogs with a long term immunity for at least about 4 months, preferably for at least about 6 months, or even more preferably, for about one year, In accordance with the present invention, a p68 vaccine can be administered to a dog by any known routes, including the oral, intranasal, mucosal, topical, transdermal, and parenteral (e.g., intravenous, intraperitoneal, intradermal, subcutaneous or intramuscular). Administration can also be achieved using needle-free delivery devices. Administration can be achieved using a combination of routes, e.g., first administration using a parental route and subsequent administration using a mucosal route.

Preferred routes of administration include subcutaneous and intramuscular administrations.

The p68 vaccine composition of the present invention can be administered to dogs of at least 6 weeks old, preferably at least 7 weeks old, and more preferably, at least 8 or 9 weeks old. Dogs can be vaccinated with one dose or with more than one dose of a p68 vaccine. Preferably, two doses of a p68 vaccine are administered to dogs with an interval of about 2-4 weeks, preferably about 3 weeks, between the two administrations. If dogs are vaccinated before the age of 4 months, it is recommended that they be revaccinated with a single dose upon reaching 4 months of age, because maternal antibodies may interfere with development of an adequate immune response in puppies less than 4 months old. Dogs can also be revaccinated annually with a single dose. Where *B. bronchiseptica* exposure is likely, such as breeding, boarding, and showing situations, an additional booster may be given within 1 year, or preferably 6 months, of the occurrence of these events.

p68 Combination Vaccines

In another embodiment, the present invention provides combination vaccines and methods for protecting dogs against *Bordetella bronchiseptica* and one or more other canine pathogens by administering such combination vaccines. The combination vaccine compositions of the present invention do not exhibit efficacy interference and are safe for administration to puppies.

The combination vaccines of the present invention include a *Bordetella bronchiseptica* p68 antigen, which can be made as described hereinabove, in combination with at least one antigen from other canine pathogens capable of inducing a protective immune response in dogs against disease caused by such other pathogens.

Such other pathogens include, but are not limited to, canine distemper (CD) virus, canine adenovirus type 2 (CAV-2), canine parainfluenza (CPI) virus, canine parvovirus (CPV), canine coronavirus (CCV), canine herpesvirus, and rabies virus. Antigens from these pathogens for use in the vaccine compositions of the present invention can be in the form of a modified live viral preparation or an inactivated viral preparation. Methods of attenuating virulent strains of these viruses and methods of making an inactivated viral preparation are known in the art and are described in, e.g., U.S. Pat. Nos. 4,567,042 and 4,567,043.

Other pathogens also include *Leptospira bratislava, Leptospira canicola, Leptospira grippotyphosa, Leptospira icterohaemorrhagiae, Leptospira pomona, Leptospira hardjobovis, Porphyromonas* spp., *Bacteriodes* spp., *Leishmania* spp., *Borrelia* spp., *Ehrlichia* spp., *Mycoplasma* ssp. and *Microsporum canis*. Antigens from these pathogens for use in the vaccine compositions of the present invention can be in the form of an inactivated whole or partial cell preparation, using methods well-known in the art. For example, methods of making an inactivated whole or partial *Leptospira* cell preparation are known in the art and are described in, e.g., Yan, K-T, "Aspects of Immunity to *Leptospira borgpetersenii* serovar hardjo", PhD Thesis, Appendix I, 1996. Faculty of Agriculture and Food Science, The Queen's University of Belfast; Mackintosh et al., "The use of a *hardjo-pomona* vaccine to prevent leptospiruria in cattle exposed to natural challenge with *Leptospia interrogans serovarhardjo*", New Zealand Vet. J. 28:174-177, 1980; Bolin et. al., "Effect of vaccination with a pentavalent leptopsiral vaccine on *Leptospira interrogans serovar hardjo type hardjo-boivs* infection of pregnant cattle", Am. J. Vet. Res. 50:161-165, 1989.

In accordance with the present invention, the combination vaccines generally include a veterinary-acceptable carrier. As described hereinabove, a veterinary-acceptable carrier includes any and all solvents, dispersion media, coatings, adjuvants, stabilizing agents, diluents, preservatives, antibacterial and antifungal agents, isotonic agents, adsorption delaying agents, and the like. Diluents can include water, saline, dextrose, ethanol, glycerol, and the like. Isotonic agents can include sodium chloride, dextrose, mannitol, sorbitol, and lactose, among others. Stabilizers include albumin, among others.

Adjuvants suitable for use in accordance with the present invention include, but are not limited to several adjuvant classes such as; mineral salts, e.g., Alum, aluminum hydroxide, aluminum phosphate and calcium phosphate; surface-active agents and microparticles, e.g., nonionic block polymer surfactants (e.g., cholesterol), virosomes, saponins (e.g., Quil A, QS-21 and GPI-0100), proteosomes, immune stimulating complexes, cochleates, quarterinary amines (dimethyl diocatadecyl ammonium bromide (DDA)), pyridine, vitamin A, vitamin E; bacterial products such as the RIBI adjuvant system (Ribi Inc.), cell wall skeleton of *Mycobacterum phlei* (Detox®), muramyl dipeptides (MDP) and tripeptides (MTP), monophosphoryl lipid A, *Bacillus* Calmete-Guerin, heat labile *E. coli* enterotoxins, cholera toxin, trehalose dimycolate, CpG oligodeoxnucleotides; cytokines and hormones, e.g., interleukins (IL-1, IL-2, IL-6, IL-12, IL-15, IL-18), granulocyte-macrophage colony stimulating factor, dehydroepiandrosterone, 1,25-dihydroxy vitamin $D_3$; polyanions, e.g., dextran; polyacrylics (e.g., polymethylmethacrylate, Carbopol 934P); carriers e.g., tetanus toxid, diptheria toxoid, cholera toxin B subnuit, mutant heat labile enterotoxin of enterotoxigenic *E. coli* (rmLT), heat shock proteins; oil-in-water emulsions e.g., AMPHIGEN® (Hydronics, USA); and water-in-oil emulsions such as, e.g., Freund's complete and incomplete adjuvants.

Preferred adjuvants for use in the combination vaccines in accordance with the present invention include Quil A and cholesterol.

The p68 antigen, one or more antigens from other pathogens, and the veterinary-acceptable carrier can be combined in any convenient and practical manner to form a combination vaccine composition, e.g., by admixture, solution, suspension, emulsification, encapsulation, absorption and the like, and can be made in formulations such as tablets, capsules, powder, syrup, suspensions that are suitable for injections, implantations, inhalations, ingestions or the like. Preferably, the vaccine is formulated such that it can be administered to dogs by injection in a dose of about 0.1 to 5 ml, or preferably about 0.5 to 2.5 ml, or even more preferably, in a dose of about 1 ml.

In accordance with the present invention, p68 combination vaccines can be administered to a dog of at least 6 weeks old, preferably at least 7 weeks old, and more preferably, at least 8 or 9 weeks old. The administration can be done by any known routes, including the oral, intranasal, mucosal topical, transdermal, and parenteral (e.g., intravenous, intraperitoneal, intradermal, subcutaneous or intramuscular). Administration can also be achieved using needle-free delivery devices. Administration can also be achieved using a combination of routes, e.g., first administration using a parental route and subsequent administration using a mucosal route. Preferred routes of administration include subcutaneous and intramuscular administrations.

Preferred p68 Combination Vaccines and Vaccination Methods

A preferred combination vaccine of the present invention includes an attenuated strain of CD virus, an attenuated strain of CAV-2, an attenuated strain of CPI virus, an attenuated strain of CPV, an inactivated preparation of a strain of CCV, and a *Bordetella bronchiseptica* p68 antigen.

An especially preferred combination vaccine includes the attenuated CD virus strain designated as the "Snyder Hill" strain (National Veterinary Service Laboratory, Ames, Iowa), the attenuated CAV-2 strain designated as the "Manhattan" strain (National Veterinary Service Laboratory, Ames, Iowa), the attenuated CPI virus strain having the designation of "NL-CPI-5" (National Veterinary Service Laboratory, Ames, Iowa), the attenuated CPV strain having the designation of "NL-35-D" (National Veterinary Service Laboratory, Ames, Iowa), an inactivated preparation of the CCV strain having the designation of "NL-18" (National Veterinary Service Laboratory, Ames, Iowa), and the recombinant *Bordetella bronchiseptica* p68 antigen having the sequence of SEQ ID NO: 1. Such combination vaccine, also referred to herein as "the p68/5CV combination vaccine", is preferably prepared by rehydrating a freeze-dried preparation of the attenuated viral strains and viral preparation with a liquid preparation, which liquid preparation is composed of the p68 antigen dissolved in sterile saline solution and adjuvanted with Quil A and cholesterol.

Another especially preferred combination vaccine includes the antigenic components of the p68/5CV combination vaccine as well as inactivated whole cell preparations of five *Leptospira* species: *Leptospira bratislava* (e.g., a *Leptospira bratislava* strain which can be obtained from National Veterinary Service Laboratory, Ames, Iowa), *Leptospira canicola* (e.g., strain C-5, National Veterinary Service Laboratory, Ames, Iowa), *Leptospira grippotyphosa* (e.g., strain MAL 1540, National Veterinary Service Laboratory, Ames, Iowa.), *Leptospira icterohaemorrhagiae* (e.g., strain NADL 11403, National Veterinary Service Laboratory, Ames, Iowa) and *Leptospira pomona* (e.g., strain T262, National Veterinary Service Laboratory, Ames, Iowa). Such combination vaccine, also referred to herein as "the p68/5CV-Leptospira combination vaccine", is preferably prepared by rehydrating a freeze-dried preparation of the attenuated viral strains (or a preparation made by other methods such as spray drying or desiccation) and viral preparation with a liquid preparation, which liquid preparation is composed of the p68 antigen and Leptospiral antigens, dissolved in sterile saline solution and adjuvanted with Quil A and cholesterol.

In accordance with the present invention, the p68/5CV and p68/5CV-Leptospira combination vaccines can be administered to healthy dogs 4 weeks of age or older, preferably 6 weeks or older, and preferably in 3 doses, each administered about 3 weeks apart. Dogs can be revaccinated annually with a single dose. Where *B. bronchiseptica* and canine virus exposure is likely, such as breeding, boarding, and showing situations, an additional booster may be given within 1 year, or preferably 6 months, of the occurrence of these events.

Still another preferred combination vaccine of the present invention includes an attenuated strain of CD virus, an attenuated strain of CAV-2, an attenuated strain of CPI virus, an attenuated strain of CPV, and a recombinant *Bordetella bronchiseptica* p68 antigen.

An especially preferred combination vaccine includes the attenuated CD virus strain designated as the "Synder Hill" strain (National Veterinary Service Laboratory, Ames, Iowa), the attenuated CAV-2 strain designated as the "Manhattan" strain (National Veterinary Service Laboratory, Ames, Iowa), the attenuated CPI virus strain having the designation of "NL-CPI-5" (National Veterinary Service Laboratory, Ames, Iowa), the attenuated CPV strain designated as "NL-35-D" (National Veterinary Service Laboratory, Ames, Iowa), and the recombinant *Bordetella bronchiseptica* p68 antigen having the sequence of SEQ ID NO: 1. Such combination vaccine, also referred to herein as "the p68/$DA_2PP$ combination vaccine", is preferably prepared by rehydrating a freeze-dried preparation of the attenuated viral strains (or a preparation made by other methods such as spray drying or desiccation) with a liquid preparation, which liquid preparation is composed of the p68 antigen dissolved in sterile saline solution and adjuvanted with Quil A and cholesterol.

Another especially preferred combination vaccine includes the antigenic components of the p68/DA$_2$PP combination vaccine as well as inactivated whole cell preparations of two *Leptospira* species: *Leptospira canicola* (e.g., strain C-51, National Veterinary Service Laboratory, Ames, Iowa), and *Leptospira icterohaemorrhagiae* (e.g., strain NADL 11403, National Veterinary Service Laboratory, Ames, Iowa). Alternatively, a preferred combination vaccine can include the antigenic components of the p68/DA$_2$PP combination vaccine as well as inactivated whole cell preparations of five *Leptospira* species: *Leptospira bratislava*, *Leptospira canicola*, *Leptospira grippotyphosa*, *Leptospira icterohaemorrhagiae* and *Leptospira pomona*. These combination vaccines, also referred to herein as "the p68/DA$_2$PP-*Leptospira* combination vaccines", are preferably prepared by rehydrating a freeze-dried preparation of the attenuated viral strains (or a preparation made by other methods such as spray drying or desiccation) and viral preparation with a liquid preparation, which liquid preparation is composed of the p68 antigen and Leptospiral antigens, dissolved in sterile saline solution and adjuvanted with Quil A and cholesterol.

In accordance with the present invention, the p68/DA$_2$PP and p68/DA$_2$PP-Leptospira combination vaccines can be administered to healthy dogs 6 weeks or older, or preferably 8 weeks of age or older, and preferably in 2 doses, each administered about 3 weeks apart. A single dose may be sufficient if given to a dog at least 12 weeks of age. Dogs can be revaccinated annually with a single dose. Where *B. bronchiseptica* and canine virus exposure is likely, such as breeding, boarding, and showing situations, an additional booster may be given within 1 year, or preferably 6 months, of the occurrence of these events. Another preferred combination vaccine include a p68 antigen, preferably the recombinant p68 antigen having SEQ ID NO: 1, in combination with an attenuated strain of CPI.

Still another preferred combination vaccine include a p68 antigen, preferably the recombinant p68 antigen having SEQ ID NO: 1, an attenuated strain of CPI, and two or more *Leptospira* species such as *Leptospira canicola* (e.g., strain C-51, National Veterinary Service Laboratory, Ames, Iowa), and *Leptospira icterohaemorrhagiae* (e.g., strain NADL 11403, National Veterinary Service Laboratory, Ames, Iowa).

The amount of the p68 antigen and the antigen(s) from one or more other pathogens in the combination vaccines of the present invention should be immunizing-effective. In general, the p68 antigen in a combination vaccine should be in an amount of at least about 0.5 µg per dose. The attenuated CD virus should be in an amount of at least about $10^2$ to about $10^9$ TCID$_{50}$ per dose TCID$_{50}$ (tissue culture infectious dose 50% cytopathic effect) per dose, and preferably in the range of about $10^4$ to about $10^6$ TCID$_{50}$ per dose. The attenuated CAV-2 should be in an amount of at least about $10^2$ TCID$_{50}$ to about $10^9$ TCID$_{50}$ per dose, preferably in the range of $10^{4.8}$ to about $10^{6.0}$ TCID$_{50}$ per dose. The attenuated CPI virus should be in an amount of at least about $10^2$ TCID$_{50}$ to about $10^9$ TCID$_{50}$ per dose, and preferably in the range of $10^6$ to about $10^8$ TCID$_{50}$ per dose. The attenuated CPV should be in an amount of at least about $10^2$ TCID$_{50}$ to about $10^9$ TCID$_{50}$ per dose, preferably, an amount in the range of $10^7$ to about $10^9$ TCID$_{50}$ per dose. The amount of CCV in an inactivated viral preparation should be at least about 100 relative units per dose, and preferably in the range of 1000-4500 relative units per dose. Each *Leptospira* species in the vaccine should be in the range of about 100-3500 NU (nephelometric units) per vaccine dose, and preferably in the range of 200-2000 NU per dose.

The combination vaccines are formulated such that the vaccines can be administered to dogs by injection in a dose of 0.1 ml to 5 ml, preferably from 0.5 ml to 2.5 ml, and more preferably, about 1 ml.

The present invention is further illustrated by the following non-limiting examples.

EXAMPLE 1

*Canine Bordetella* p68 Recombinant Antigen Dose Titration Study

Vaccine:

The experimental vaccine antigen was a recombinant p68 outer membrane protein (SEQ ID NO: 1) of *B. bronchiseptica* produced by *E. coli* strain LW68. The vaccine contained varying levels of SDS (sodium dodecyl sulfate) solubilized p68, adjuvanted with 50 µg of QAC (Quil A/50 µg cholesterol) in a 1 mL dose.

Challenge Material:

An aerosol of *Bordetella bronchiseptica*, dog isolate #85B, passage #3, lot #051597, was used as the challenge material. The mean plate count was $1.59 \times 10^8$ CFU/ml.

Animals:

Sixty male and female canine pups were randomly allocated to one of six treatment groups (10 pups per group). Pups were bled and tracheal swabs were taken 41 days prior to the first vaccination and again 28 days prior to first vaccination and any seropositive or culture positive animals were removed from the study.

Animals were randomly assigned to treatments and rooms according to a randomized complete block design. Post-vaccination observations were done without knowledge of vaccine assignment groups.

Design

| Group | Dose Level | Route[1] | Number of Animals |
| --- | --- | --- | --- |
| T01 | Saline Control (0.9% saline as a 1 mL dose) | SC | 9 |
| T02 | 1 µg p68 | SC | 8 |
| T03 | 4 µg p68 | SC | 8 |
| T04 | 16 µg p68 | SC | 9 |
| T05 | 64 µg p68 | SC | 9 |
| T06 | 256 µg p68 | SC | 9 |

[1]SC = subcutaneous

Procedure

IVP Administration:

Animals were vaccinated on Day 0 with either the placebo or the experimental vaccine. A second vaccination was administered on Day 21. The first vaccination was administered subcutaneously in the right neck and the second vaccination was administered subcutaneously in the left neck.

Challenge Administration:

All animals were challenged 28 days after the second vaccination with an aerosol of *Bordetella bronchispetica*. Animals were monitored for coughing for a period of 30 minutes, twice daily (once in the a.m. and once in the p.m.) on days two through fourteen following challenge (Days 51 through 63).

Observations and Samples Collection:

All injection sites were palpated and measured three dimensionally for seven days following each vaccination (Days 0 through 7 and 21 through 28) and on the 14$^{th}$ day post each vaccination (Days 14 and 35).

Rectal temperatures were recorded on the day of vaccination and for three days following each vaccination (Days 0 through 3 and 21 through 24).

Blood was collected on the days of vaccination (Days 0 and 21) and on Days 42, 50, and 63 and assayed by ELISA for specific antibodies against the p68 protein purified from *B. bronchispetica*. Blood was also collected on Days 42, 49, 50, 52, 54, 56 and 58 and analyzed for Serum Amyloid A (SAA).

All animals were tracheal swabbed for *B. bronchispetica* isolation and blood was collected for *B. bronchispetica* agglutination titers prior to vaccination (at the vendor, on Day-41 and Day-28) and on Day 49.

*Bordetella* P68 Dog and Mouse Antibody Titration DAB ELISA

Purified native p68 was diluted to 600 ng/mL in 0.01 M Borate Buffer and was added to each well at 100 µL/well. The plates were incubated overnight at 4° C. The plates were then washed once with excess PBS-Tween 20.1% nonfat dried milk in PBS was added to the plates at 200 µL/well. The plates were then incubated for 1 hour at 37° C. The plates were then washed once with excess PBS-Tween 20.

Dog or mouse serum was added at a 1:50 dilution to the top row of the ELISA plates and two fold serially diluted serum was added all the way down the plate. The plates were incubated for 1 hour at 37° C. Subsequently, the plates were washed 3 times with excess PBS-Tween 20.

To plates incubated with dog serum above, peroxidase labeled goat anti-dog IgG (H+L), diluted at a 1:2000 dilution, was added at 100 µL/well. The plates were then incubated for 1 hour at 37° C. To plates incubated with mouse serum above, peroxidase labeled goat anti-mouse IgG (H+ L), diluted at a 1:4000 dilution, was added at 100 µL/well. The plates were then incubated for 1 hour at 37° C. The plates were then washed 3 times with excess PBS-Tween 20.

ABTS substrate was added at 100 µL/well. Approximately 20 minutes later, the plates were read with a Molecular Devices or an equivalent plate reader at 405-490 nm.

Data Analysis

Treatment differences in the number of dogs coughing were tested using Fisher's Exact Test. The 5% level of significance was used.

ELISA titers were log transformed prior to analysis using a general linear mixed model. The 95% level of confidence was used to assess treatment differences. Challenge observations were monitored twice daily for 30 minutes each.

Results

Tracheal Swab Culture and Agglutination Titers

Tracheal swab cultures and agglutination titers were evaluated to monitor the *B. bronchiseptica* status of animals enrolled in the study. A number of dogs demonstrated increased titers at various time points but no titer increased above 128 prior to challenge.

Injection Site Observations

Injection site reactions following the first vaccination are presented in Table 1. The largest injection site reactions were observed in T05 (64 µg) vaccinated animals, with the largest mean injection site reaction measuring only 14.69 cm³ (two days post vaccination). T03 (4 µg), T04 (16 µg) and T06 (256 µg) vaccinated animals demonstrated varying injection site reactions up to 7 days post vaccination. T02 (1 µg) vaccinated animals only demonstrated reactions on Day 1 post vaccination. By the seventh day post vaccination, there was no statistically significant difference in injection site reactions among the treatment groups. By Day 14, all injection site reactions had dissipated.

Injection site reactions following the second vaccination are presented in Table 2. Following the second vaccination the largest mean injection site reactions were observed in T06 (256 µg), with the largest mean injection site reaction measuring 50.03 cm³ (one day post vaccination). Injection site reactions were demonstrated in T05 (64 µg) and T04 (16 µg) animals up to 7 days post second vaccination. Minimal injection site reactions were demonstrated in T03 (0.4 µg) and T02 (0.1 µg) animals up to 7 days post vaccination. Injection site reactions that were not statistically different from the placebo group were demonstrated in T02 (0.1 µg) and T03 (0.4 µg) post vaccination. Fourteen days post second vaccination no injection site reactions were observed.

Frequency of injection site reactions following first vaccination is presented in Table 3. The highest overall LSM frequency, 76%, of injection sites exhibiting a reaction at any time post first vaccination resulted from vaccination with T06 (25.6 µg). The next most frequent were 72% of the injection sites showing a reaction following the first vaccination with T05 (6.4 µg), 69% following the first vaccination with T04 (16 µg), and 63% following the first vaccination with T03 (0.4 µg). The lowest frequency, 38%, followed the first vaccination of T02 (0.1 µg).

Frequency of injection site reactions following the second vaccination is presented in Table 4. The overall LSM frequency for each vaccine was consistent with that seen post first vaccination.

Incidence and duration of injection site reactions following vaccination are summarized in Table 5. The incidence (or the number of dogs showing a reaction at any time) of a measurable injection site reaction was 100% for T03, T04, T05 and T06 (0.4 µg, 16 µg, 64 µg, and 256 µg, respectively) following the first and second vaccination. Animals that received T02 (0.1 µg) demonstrated the least incidence of injection site reactions post vaccination (57.1%).

Duration of the reaction (expressed as a least squares means of days with a reaction shown in Table 5) was longer for T04, T05 and T06 (16 µg, 64 µg, and 256 µg, respectively) vaccinated animals following the first and second vaccinations (2.7 to 5.1 days post first vaccination and 6.0 to 6.7 days post second vaccination). T02 and T03 (0.1 µg and 0.4 µg, respectively) vaccinated animals demonstrated the fewest number of days with an injection site reaction following the first and second vaccinations (0.3 and 1.3 days post first vaccination and 1.9 and 4.5 days post second vaccination).

Rectal Temperatures

Mean rectal temperature measurements are summarized in Table 6. The LSM rectal temperature for T02 (1 µg) on Day 1 and 24, for T03 (4 µg) on Day 1, 21, and 24, for T04 (16 µg) on Day 2 and 24, for T05 (64 µg) on Day 23, and for T06 (256 µg) on Day 0, 1, and 24 were significantly different from the placebo. On Day 23 all comparisons were not statistically significant (P>0.05) from the placebo.

p68 ELISA Serology

Summary of p68 ELISA data are presented in Table 7. The pre-vaccination geometric mean virus titers of p68 ELISA specific antibodies in all groups were low (range 24.9 to 28.9) and titers for the placebo remained low throughout the duration of the study. Twenty-one days following the first vaccination, p68 ELISA geometric mean titers had increased in the vaccinated treatment (range 55.2 to 4,411.7), however T02 (1 µg) titer was not statistically different from the Placebo (T01). Forty-two days after the second vaccination, geometric mean titers were further increased in all vaccinated groups (range 674.6 to 48,382.0) demonstrating good serological response to vaccination.

Serum Amyloid A (SAA) Serology

SAA titers are summarized in Table 8. Prior to challenge, geometric mean SAA titers were low in all the treatment groups (range 0.1 to 0.5). Post challenge, T01 GMT titers ranged from 1.5 to 146.0, where p68 treatment groups ranged from 0.3 to 23.1. All treatment groups were statistically different than the placebo on Days 50, 52, 54, and 56. No statistical differences were demonstrated among the p68 vaccines with the exception of T02 (1 µg) on Day 52 when it demonstrated a statistically different geometric mean from all other p68 treatment groups.

Challenge Response

Challenge response data are presented in Table 9. The response was determined by monitoring coughing following challenge and the observations were analyzed using two methods: least square mean number of days with cough and two consecutive days of coughing (Incidence of Disease).

Analysis of the mean number of days coughing demonstrated no statistically significant difference between the p68 treatment groups; but in the dogs vaccinated with placebo coughed a mean of 8.6 days whereas dogs administered p68 vaccines coughed significantly less, means ranging between 2.2 to 4.7 days.

When dogs were evaluated using Incidence of Disease, all T01 (placebo) were observed coughing for two consecutive days (100% Incidence of Disease). T04 (16 µg) and T05 (64 µg) vaccinated dogs demonstrated an Incidence of Disease of 55.6% and 66.7%, respectively. Only 28.6% of T02 (1 µg), 50% of T03 (4 µg), and 33.3% of T06 (256 µg) vaccinated dogs were observed coughing for two consecutive days.

Discussion

In this study, the objective was to establish a relationship between antigen dose, immune response, and protection in dogs. The p68 antigen doses examined were 0.1 µg, 4 µg, 16 µg, 64 µg, and 256 µg.

Analysis of injection site reaction measurements demonstrated a negligible reaction in the p68 treatment groups, with the exception of T06 (256 µg) on the first day post second vaccination. Reactions that were observed tended to be small, generally decreasing in size during the observation periods. The size of these reactions was clinically insignificant and would most likely go unnoticed on unshaven dogs.

Rectal temperatures post vaccination were unremarkable and were within normal limits for all dogs in all groups.

Serological response to vaccination was excellent in T03 through T06 groups. In these treatment groups, all demonstrated significantly higher p68 ELISA titers when compared to the placebo from Day 21 through Day 63. T02 (1 µg) demonstrated significant p68 ELISA titers compared to the T01 (placebo) from Day 42 through Day 63. The highest titers were observed in T05 (64 µg) and T06 (256 µg).

Examination of the SAA response in all p68 vaccinated dogs following challenge indicated a much smaller rise in the SAA post-challenge when compared to control dogs. No difference was demonstrated between the p68 vaccine dose levels post-challenge with the exception of T02 (0.1 µg) on Day 52 that demonstrated a statistically different geometric mean from all other p68 treatment groups.

Post challenge coughing observations were analyzed using least squares means (LSM) of the number of days with cough or two consecutive days coughing (incidence of disease). Using LSM of days coughing, a significant difference was demonstrated between placebo and all p68 vaccinated groups although no difference was demonstrated between the different p68 vaccine dose levels. Using the Incidence of Disease T02 (1 µg), T03 (4 µg) and T06 (256 µg) vaccinated dogs coughed significantly less than the placebo.

Conclusions

The study was conducted to establish a relationship between antigen dose, immune response, and protection in dogs. The p68 antigen doses examined were 0.1 µg, 0.4 µg, 16 µg, 64 µg, and 256 µg.

All vaccines were safe as demonstrated by minimal injection site reactions, normal rectal temperatures and absence of adverse response to vaccination. The size of the injection site reactions and the duration of these reactions were less in the lower antigenic treatment groups. Serological response to vaccination as measured by ELISA titers was excellent with the higher antigenic dose groups demonstrating higher serological responses. When using LSM days coughing as a method of comparison, all treatment groups demonstrated a significant reduction in coughing when compared to placebo. No differences were noted between the treatment groups. When two consecutive days coughing (or Incidence of Disease) was used for comparison, T02 (0.1 µg), T03 (0.4 µg) and T06 (256 µg) vaccinated dogs coughed significantly less than the placebo.

TABLE 1

Volume of Injection Site Reaction in Dogs Following First Vaccination with p68 Antigen or Placebo

| Treatment (N) | LS Mean Size (cm$^3$) of Injection Site Reactions After First Vaccination by Day of Study[1]: | | | | | | | | |
|---|---|---|---|---|---|---|---|---|---|
| | 0 | 1 | 2 | 3 | 4 | 5 | 6 | 7 | 14 |
| T01 Placebo (9) | 0.00$^a$ | 0.00$^a$ | 0.00$^a$ | 0.00$^a$ | 0.00$^a$ | 0.00$^a$ | 0.00$^a$ | 0.00$^a$ | 0.00$^a$ |
| T02 p68, 1 µg (7) | 0.00$^a$ | 4.00$^b$ | 0.00$^{a,b}$ | 0.00$^a$ | 0.00$^a$ | 0.00$^a$ | 0.00$^{a,b}$ | 0.00$^a$ | 0.00$^a$ |
| T03 p68, 4 µg (8) | 0.00$^a$ | 0.00$^{a,c}$ | 0.64$^{a,b}$ | 4.56$^b$ | 1.14$^{a,b}$ | 0.39$^a$ | 0.00$^a$ | 0.00$^a$ | 0.00$^a$ |
| T04 p68, 16 µg (9) | 0.00$^a$ | 0.00$^a$ | 3.56$^b$ | 4.28$^b$ | 1.32$^{a,b}$ | 1.79$^{a,b}$ | 2.36$^{a,b}$ | 0.38$^a$ | 0.00$^a$ |
| T05 p68, 64 µg (9) | 0.00$^a$ | 10.44$^d$ | 14.69$^c$ | 10.56$^c$ | 4.01$^{b,c}$ | 4.40$^b$ | 2.82$^{a,b}$ | 1.15$^a$ | 0.00$^a$ |
| T06 p68, 256 µg (9) | 0.00$^a$ | 7.00$^e$ | 8.53$^d$ | 7.50$^{b,c}$ | 5.62$^c$ | 4.36$^b$ | 3.56$^b$ | 1.24$^a$ | 0.00$^a$ |

TABLE 2

Volume of Injection Site Reaction Following Second Vaccination with p68 Antigen or Placebo

| | | LS Mean Size (cm$^3$) of Injection Site Reactions After Second Vaccination by Day of Study[1]: | | | | | | | | |
|---|---|---|---|---|---|---|---|---|---|---|
| | Treatment (N) | 0 (21) | 1 (22) | 2 (23) | 3 (24) | 4 (25) | 5 (26) | 6 (27) | 7 (28) | 14 (35) |
| T01 | Placebo (9) | 0.00$^a$ | 0.00$^a$ | 0.00$^a$ | 0.00$^a$ | 0.00$^a$ | 0.00$^a$ | 0.00$^a$ | 0.00$^a$ | 0.00$^a$ |
| T02 | p68, 1 µg (7) | 0.00$^a$ | 0.54$^a$ | 2.36$^{a,b}$ | 1.14$^a$ | 0.45$^a$ | 0.61$^a$ | 0.50$^a$ | 0.16$^a$ | 0.00$^a$ |
| T03 | p68, 4 µg (8) | 0.00$^a$ | 0.00$^a$ | 5.33$^{a,b,c}$ | 4.20$^a$ | 2.59$^{a,b}$ | 2.89$^{a,b}$ | 1.53$^a$ | 1.23$^{a,b}$ | 0.00$^a$ |
| T04 | p68, 16 µg (9) | 0.00$^a$ | 0.00$^a$ | 7.58$^{b,c}$ | 10.67$^b$ | 7.25$^{b,c}$ | 7.28$^c$ | 7.97$^b$ | 5.14$^{a,b}$ | 0.00$^a$ |
| T05 | p68, 64 µg (9) | 0.00$^a$ | 2.89$^a$ | 10.99$^c$ | 14.28$^b$ | 9.79$^c$ | 9.75$^c$ | 11.14$^b$ | 6.50$^b$ | 0.00$^a$ |
| T06 | p68, 256 µg (9) | 0.00$^a$ | 50.03$^b$ | 8.58$^{b,c}$ | 13.44$^b$ | 11.32$^c$ | 7.42$^{b,c}$ | 9.51$^b$ | 2.69$^{a,b}$ | 0.00$^a$ |

[1]Values with different superscripts are statistically different ($P \leq 0.05$)

TABLE 3

Frequency of Injection Site Reaction Following First Vaccination with p68 Antigen or Placebo

| | | LS Mean Percent Dogs per Pen[2] with Reaction After First Vaccination by Day of Study[3]: | | | | | | | | |
|---|---|---|---|---|---|---|---|---|---|---|
| | Treatment (N) | 0 | 1 | 2 | 3 | 4 | 5 | 6 | 7 | 14 |
| T01 | Placebo (9) | 0.00$^a$ | 0.00$^a$ | 0.00$^a$ | 0.00$^a$ | 0.00$^a$ | 0.00$^a$ | 0.00$^a$ | 0.00$^a$ | 0.00$^a$ |
| T02 | p68, 1 µg (7) | 0.00$^a$ | 100.00$^b$ | 83.33$^b$ | 50.00$^b$ | 25.00$^a$ | 12.50$^b$ | 37.50$^b$ | 37.50$^b$ | 0.00$^a$ |
| T03 | p68, 4 µg (8) | 0.00$^a$ | 90.00$^{b,c}$ | 80.00$^b$ | 90.00$^c$ | 80.00$^b$ | 63.33$^b$ | 80.00$^c$ | 80.00$^c$ | 0.00$^a$ |
| T04 | p68, 16 µg (9) | 0.00$^a$ | 62.50$^c$ | 87.50$^b$ | 100.00$^c$ | 100.00$^b$ | 77.50$^{b,c}$ | 87.50$^c$ | 100.00$^c$ | 10.00$^a$ |
| T05 | p68, 64 µg (9) | 0.00$^a$ | 90.00$^{b,c}$ | 100.00$^b$ | 100.00$^c$ | 90.00$^b$ | 90.00$^{b,c}$ | 90.00$^c$ | 90.00$^c$ | 0.00$^a$ |
| T06 | p68, 256 µg (9) | 0.00$^a$ | 100.00$^{b,d}$ | 100.00$^b$ | 100.00$^c$ | 100.00$^b$ | 100.00$^c$ | 87.50$^c$ | 100.00$^c$ | 0.00$^a$ |

TABLE 4

Frequency of Injection Site Reaction Following Second Vaccination with p68 Antigen or Placebo

| | | LS Mean Percent Dogs per Pen[1] with Reaction After Second Vaccination by Day of Study[2]: | | | | | | | | |
|---|---|---|---|---|---|---|---|---|---|---|
| | Treatment (N) | 0 (21) | 1 (22) | 2 (23) | 3 (24) | 4 (25) | 5 (26) | 6 (27) | 7 (28) | 14 (35) |
| T01 | Placebo (9) | 0.00$^a$ | 0.00$^a$ | 20.00$^a$ | 10.00$^a$ | 0.00$^a$ | 0.00$^a$ | 0.00$^a$ | 0.00$^a$ | 0.00$^a$ |
| T02 | p68, 1 µg (7) | 0.00$^a$ | 58.33$^b$ | 58.33$^b$ | 58.33$^b$ | 45.83$^b$ | 41.67$^b$ | 41.67$^b$ | 29.17$^b$ | 0.00$^a$ |
| T03 | p68, 4 µg (8) | 0.00$^a$ | 83.33$^c$ | 100.00$^c$ | 100.00$^c$ | 90.00$^c$ | 73.33$^c$ | 73.33$^c$ | 73.33$^c$ | 0.00$^a$ |
| T04 | p68, 16 µg (9) | 0.00$^a$ | 90.00$^{c,d}$ | 100.00$^c$ | 100.00$^c$ | 100.00$^c$ | 100.00$^d$ | 100.00$^d$ | 100.00$^d$ | 0.00$^a$ |
| T05 | p68, 64 µg (9) | 0.00$^a$ | 100.00$^d$ | 100.00$^c$ | 100.00$^c$ | 100.00$^c$ | 100.00$^d$ | 100.00$^d$ | 100.00$^d$ | 0.00$^a$ |
| T06 | p68, 256 µg (9) | 0.00$^a$ | 100.00$^d$ | 100.00$^c$ | 100.00$^c$ | 100.00$^c$ | 100.00$^d$ | 100.00$^d$ | 87.50$^{c,d}$ | 0.00$^a$ |

[2]Two pens per treatment
[3]Values with different superscripts are statistically different ($P \leq 0.05$).

TABLE 5

Duration of Injection Site Reactions Following Vaccination with p68 Antigen or Placebo

| Treatment (N) | Measurable Reaction (anytime) | LS Mean Days with Reaction[4] (post first vaccination) | LS Mean Days with Reaction[1] (post second vaccination) |
|---|---|---|---|
| T01 Placebo (9) | 0/9 (0%) | 0.0$^a$ | −0.0$^a$ |
| T02 p68, 1 µg (7) | 4/7 (57.1%) | 0.3$^a$ | 1.9$^b$ |
| T03 p68, 4 µg (8) | 8/8 (100%) | 1.3$^{a,b}$ | 4.5$^c$ |
| T04 p68, 16 µg (9) | 9/9 (100%) | 2.7$^b$ | 6.0$^d$ |
| T05 p68, 64 µg (9) | 9/9 (100%) | 4.9$^c$ | 6.3$^d$ |
| T06 p68, 256 µg (9) | 9/9 (100%) | 5.1$^c$ | 6.7$^d$ |

[4]Values with different superscripts are statistically different ($P \leq 0.05$).

TABLE 6

Mean Rectal Temperatures for Dogs Following Vaccination with p68 Antigen or Placebo

| | LS Mean Rectal Temperature by Day of Study[5] | | | | | | | |
|---|---|---|---|---|---|---|---|---|
| Treatment (N) | 0 | 1 | 2 | 3 | 21 | 22 | 23 | 24 |
| T01 Placebo (9) | $38.9^{a,b}$ | $38.9^a$ | $38.9^{a,b}$ | $39.0^a$ | $39.0^a$ | $38.8^a$ | $38.9^{a,b}$ | $39.0^a$ |
| T02 p68, 1 μg (7) | $39.0^{a,b}$ | $38.5^b$ | $38.8^a$ | $38.4^b$ | $38.7^a$ | $38.6^a$ | $38.7^{a,b}$ | $38.6^{b,c}$ |
| T03 p68, 4 μg (8) | $39.0^a$ | $38.7^{a,b}$ | $38.6^a$ | $39.0^a$ | $38.6^a$ | $38.6^a$ | $38.6^a$ | $38.4^c$ |
| T04 p68, 16 μg (9) | $39.0^a$ | $39.0^a$ | $38.9^b$ | $38.7^{a,b}$ | $38.7^a$ | $38.8^a$ | $38.7^{a,b}$ | $38.6^{b,c}$ |
| T05 p68, 64 μg (9) | $38.9^{a,b}$ | $38.9^a$ | $38.9^{a,b}$ | $38.8^a$ | $38.7^a$ | $38.7^a$ | $39.0^b$ | $38.7^{a,b}$ |
| T06 p68, 256 μg (9) | $38.7^b$ | $39.3^c$ | $38.8^{a,b}$ | $39.0^a$ | $38.8^a$ | $38.8^a$ | $38.9^{a,b}$ | $38.6^{b,c}$ |

TABLE 7

Serology p68 DAB ELISA Titers in Dogs Following Vaccination with p68 Antigen or Placebo[6]

| | Geometric Mean Virus Titers for p68 ELISA by Day of Study[2]: | | | | |
|---|---|---|---|---|---|
| Treatment (N) | 0 | 21 | 42 | 49 | 63 |
| T01 Placebo (9) | $25.2^a$ | $48.3^a$ | $30.0^a$ | $28.2^a$ | $230.4^a$ |
| T02 p68, 1 μg (7) | $25.5^a$ | $55.2^a$ | $674.6^b$ | $294.4^b$ | $1301.7^b$ |
| T03 p68, 4 μg (8) | $25.3^a$ | $310.9^b$ | $7865.0^c$ | $4414.8^c$ | $10580.1^c$ |
| T04 p68, 16 μg (9) | $28.9^a$ | $515.4^b$ | $12180.4^c$ | $5824.4^c$ | $11429.3^c$ |
| T05 p68, 64 μg (9) | $25.3^a$ | $1699.5^c$ | $36460.6^d$ | $17593.9^d$ | $22689.3^{c,d}$ |
| T06 p68, 256 μg (9) | $24.9^a$ | $4411.7^d$ | $48382.0^d$ | $25980.9^d$ | $30594.3^d$ |

[1]Vaccinations were administered on Study Days 0 and 21. Values with different superscripts are statistically different ($P \leq 0.05$)
[6]Vaccinations were administered on Study Days 0 and 21 and challenge was administered on Study Day 49.
[2]Values with different superscripts are statistically different ($P \leq 0.05$)

TABLE 8

Serum Amyloid A (SAA) Titers in Dogs Following Challenge of Dogs Vaccinated with p68 Antigen or Placebo

| | Geometric Mean Serum Amyloid A Titers by Day of Study Postchallenge[7]: | | | | | |
|---|---|---|---|---|---|---|
| Treatment (N) | 49 | 50 | 52 | 54 | 56 | 58 |
| T01 Placebo (9) | $0.2^a$ | $146.0^a$ | $87.2^a$ | $153.6^a$ | $14.7^a$ | $1.5^a$ |
| T02 p68, 1 μg (7) | $0.2^a$ | $8.3^b$ | $1.2^b$ | $0.7^b$ | $0.6^b$ | $0.3^a$ |
| T03 p68, 4 μg (8) | $0.2^a$ | $9.9^b$ | $6.4^c$ | $2.3^b$ | $1.2^b$ | $1.8^a$ |
| T04 p68, 16 μg (9) | $0.1^a$ | $16.3^b$ | $11.6^c$ | $3.0^b$ | $1.6^b$ | $1.4^a$ |
| T05 p68, 64 μg (9) | $0.5^a$ | $11.4^b$ | $8.0^c$ | $3.4^b$ | $1.3^b$ | $1.2^a$ |
| T06 p68, 256 μg (9) | $0.5^a$ | $23.1^b$ | $16.4^c$ | $3.8^b$ | $1.1^b$ | $0.4^a$ |

TABLE 9

Incidence and Duration of Coughing in Dogs Following Challenge of Dogs Vaccinated with p68 Antigen or Placebo

| Treatment (N) | Incidence of Disease[8,2] | LS Mean Days with Cough[2] |
|---|---|---|
| T01 Placebo (9) | $9/9^a$ (100%) | $8.6^a$ |
| T02 p68, 1 μg (7) | $2/7^b$ (28.6%) | $2.2^b$ |
| T03 p68, 4 μg (8) | $4/8^b$ (50%) | $3.8^b$ |
| T04 p68, 16 μg (9) | $5/9^{a,b}$ (55.6%) | $3.7^b$ |
| T05 p68, 64 μg (9) | $6/9^{a,b}$ (66.7%) | $4.7^b$ |
| T06 p68, 256 μg (9) | $3/9^b$ (33.3%) | $3.0^b$ |

[1]Value with different superscripts are statistically different ($P \leq 0.05$)
[8]Based on two consecutive days coughing.
[2]Values with different superscripts are statistically different ($P \leq 0.05$)

EXAMPLE 2

Canine *Bordetella* p68 Immunogenicity Study

Animals

Forty-five male and female mixed breed dogs were purchased. A MLV parvovirus vaccine was administered to all puppies on the day the puppies arrived at the study site. No other vaccines, other than the experimental products, were administered to the puppies during the study. Dogs were approximately 9 weeks of age (±1 week) on Day 0 (day of first vaccination).

Dogs were kept in an isolation facility necessary to prevent exposure to *Bordetella* and other canine pathogens prior to challenge. After aerosol challenge with *Bordetella*, isolation procedures were continued to prevent exposure to other canine pathogens.

Vaccines

Sterile saline was used as a placebo vaccine in treatment groups T01 and T02. Canine recombinant p68 *Bordetella Bronchiseptica* Vaccine was used in treatment groups T03 and T04. The structural gene of the p68 antigen was cloned in *Escherichia coli* and expression of the gene was regulated by a temperature sensitive promoter. The cells were lysed and the inclusion bodies were separated by centrifugation. The recombinant p68 in the inclusion bodies was solubilized by SDS treatment. The recombinant p68 (15 μg per mL) was combined with 50 μg of Quil A and 50 μg of cholesterol per mL in sterile saline as the diluent. Each one mL dose contained 0.28% of ethanol and 0.01% thimerosal.

Challenge Inoculum

*Bordetella bronchiseptica* Bihr Cat strain was prepared as the challenge inoculum using the method currently employed by Biologics Control Laboratories-Microbiology. Bordet-Genou agar plates were plated with a confluent growth of *Bordetella bronchiseptica*—Bihr Cat strain and incubated for 48 hours at 37.5+/−2.5° C. Virulent phase I colonies were selected and streaked on Bordet-Genou agar and incubated for 24 hours at 37.5+/−2.5° C. After incubation, *Bordetella* saline was used to wash colonies from the agar and the antigen was diluted to an optical density of 0.80 at 600 nm. A cell count was performed pre- and post-challenge for confirmation of the nephelometer reading. Challenge target concentration was approximately $1 \times 10^9$ CFU. The pre-challenge concentration was $2.37 \times 10^9$ CFU (100% Phase I) and post-challenge concentration count was $1.35 \times 10^9$ CFU (100% Phase I).

Study Design

SUMMARY TABLE

| Treatment Group | Treatment | Route | Number of Animals |
|---|---|---|---|
| T01 | Saline Control | Intramuscular | 8 |
| T02 | Saline Control | Subcutaneous | 7 |
| T03 | p68 15 μg/dose | Subcutaneous | 15 |
| T04 | p68 15 μg/dose | Intramuscular | 15 |

Randomization/Blinding

For the time period from vaccination to day of challenge, animals were assigned to treatments according to a generalized block design. Treatments were randomly assigned to rooms. On the day of challenge, animals were randomly assigned to challenge rooms by block.

Qualified individuals, unaware of the assigned treatment groups, conducted microbiological and serological assays and assessments of injection sites, measurements of rectal temperatures, and observations of coughing.

Data Analysis

Post vaccination response variables consisted of injection site data, rectal temperatures and p68 ELISA titers. Injection site data was summarized in the following ways: 1) number of animals having a measurable reaction by treatment and day of study, 2) number of animal time points having a measurable reaction by treatment, 3) number of animals having a measurable reaction at any time point by treatment.

Separately for first and second vaccinations, injection site volume (cubic cm), rectal temperatures and natural log transformed p68 ELISA titer data was analyzed using a general linear mixed model.

A priori linear contrasts of the treatment by observation time-point least squares mean were constructed to test treatment group differences at each observation time-point and to compare time-points within each treatment. The 5% level of significance was used for all comparisons.

Post challenge response variables consisted of daily coughing observations, p68 ELISA titers and serum amyloid A titers. Number of days coughing during the post challenge period was analyzed using a general linear mixed model.

A priori contrasts of the treatment least squares mean was constructed to test treatment group differences. The 5% level of significance was used for all comparisons.

Separately for first and second vaccinations, Fisher's Exact test was used to compare treatment groups for the incidence of two days of consecutive coughing. The 5% level of significance was used for all comparisons.

For serum amyloid A (SAA) titer data post challenge, the natural log transformation was applied to titer values prior to analysis using a general linear mixed model.

A priori linear contrasts of the treatment by observation time-point least squares mean was constructed to test treatment group differences at each observation time-point and to compare time-points within each treatment. The 5% level of significance was used for all comparisons.

Study Procedure

Detailed Animal Procedures

Forty-five (45) seronegative and culture negative pups were randomly assigned to one of 4 treatment groups. Eight and seven dogs were allocated to the intramuscular (IM) or subcutaneous (SC) control groups respectively, for a total of 15 control dogs. Fifteen dogs were allocated to the p68 SC treatment group and 15 dogs were allocated to the p68 IM treatment group. Treatment Groups are detailed in the Study Design Section above.

Day 0 was designated as the day of first vaccination. Vaccinations were administered on Day 0 and repeated 21 days later. For the first vaccination, the right side of the neck was used and for the second vaccination, the left side of the neck was used. Intramuscular injections were administered in the right and left semimembranosus muscle for the first and second vaccinations, respectively. All injection sites were measured three dimensionally for seven days following each vaccination with a follow-up measurement conducted 14 days following vaccination. Rectal temperatures were monitored on the day of vaccination (prior to vaccination) and for three days following each vaccination.

On Day 35, all animals were tracheal swabbed for *B. bronchiseptica* culture and blood was collected for agglutination titers. All animals were negative by tracheal swab and serologically negative to *Bordetella* and deemed eligible for challenge.

On Day 45, twenty-four days after the second vaccination, an aerosol challenge of *B. bronchiseptica* was administered to all dogs. Sedated dogs were challenged using a disposable nose cone, which was fitted snugly over the muzzle of the sedated dog. The nose cone was attached to a nebulizer which was attached to a vacuum pressure pump set at 5.5 to 6.0 psi. One mL of challenge material was placed in the nebulizer and the aerosolized challenge material was administered to each dog for 4 minutes. Personnel making observations were unaware of treatment group assignments.

Animals were monitored for coughing for 14 days following challenge (Days 46-59). Observations were made in 2 (two), approximately 30-minute periods at approximately the same time each day, one conducted in the AM and one in the PM and results were recorded.

Blood Collection

Blood for agglutination titers was collected prior to first vaccination and prior to challenge. Blood for anti-p68 ELISA evaluation was collected prior to vaccination on Days 0 and 21 and on Days 35, 45, and 59. Blood for Serum Amyloid A (SAA) assay was collected on the day of challenge (Day 45) and on Days 46, 48, 50, 52 and 54.

Tests Performed on Samples

Tracheal swabs were evaluated for the presence of *B. bronchiseptica* by culture. Each tracheal swab was streaked onto a *Bordetella* Selective Agar plate. Positive and negative controls were included. The plates were incubated at 37.5±2.5° C. for 48±4 hours. The resulting colonies on each plate were compared to the positive control and any colony which appeared identical to the positive control was further tested to confirm the presence of *B. bronchiseptica*. Conformational testing included the use of TSI, Citrate and Urea Agar and Nitrate Red media.

Sera were evaluated for agglutination titers, p68 ELISA analysis or SAA analysis using the following methods:

Agglutination titers—Sera were serially diluted in microtiter plates using *Bordetella* saline. Positive and negative controls were included on each plate. *B. bronchiseptica* Strain 87 (grown on Bordet Genou agar, harvested, inactivated and diluted to 20% T at 630 nm) was used as the agglutinating antigen and was added to each well. Plates were shaken and incubated at 35±2° C. for 2 hours. Plates were read after a second incubation at room temperature for 22 hours. The endpoint titer was determined using the last well to show 50% agglutination.

p68 ELISA titers—The recombinant p68 antigen was captured on a 96 well microtiter plate coated with a polyclonal antiserum specific to the *Bordetella* p68 antigen. Serial two-fold dilutions of the canine serum were added to the plate and incubated. Positive and negative controls at a 1:1000 dilution were included on each plate. A peroxidase labeled affinity purified goat anti-dog IgG indicator conjugate was used to detect antibodies specific for the p68 antigen. A chromogenic substrate ABTS was then added and the plate read when the positive control wells had an O.D. of 1.2±0.2. The titer of a given sample was calculated as the reciprocal of the last dilution with an optical density greater than the mean of the negative control serum dilution plus five standard deviations.

SAA titers—The canine Serum Amyloid A titers were evaluated using a kit purchased from Accuplex Co., University of Nebraska Medical Center, Omaha, Nebr. 68198. Briefly, canine SAA was captured on a microtiter plate coated with a monoclonal anti-canine SAA antibody. Diluted samples of the canine serum were added to the plate followed by a biotin labeled anti-canine antibody conjugate. Following incubation, a peroxidase conjugated streptavidin chromogenic substrate was added. The plate was read after 30 minutes.

Results

Rectal Temperatures

Summary of rectal temperature measurements are presented in Tables 10 and 11.

TABLE 10

Least squares mean of rectal temperatures (° C.) in dogs following saline or p68 *Bordetella* vaccination (post first vaccination[a])

| Treatment | Rectal Temperatures (° C.) Day of Study | | | | Std Error |
|---|---|---|---|---|---|
| | 0 | 1 | 2 | 3 | |
| T01 saline IM | 38.2 | 38.2 | 38.2 | 38.2 | 0.08 |
| T02 saline SC | 38.0 | 38.3 | 38.2 | 38.2 | 0.09 |
| T03 p68 SC | 38.1 | 38.3 | 38.1 | 38.0 | 0.06 |
| T04 p68 IM | 38.2 | 38.4 | 38.2 | 38.2 | 0.06 |

[a]First vaccination administered on Day 0.

TABLE 11

Least squares mean of rectal temperatures (° C.) in dogs following saline or p68 *Bordetella* vaccination (post second vaccination[a])

| Treatment | Rectal Temperatures (° C.) Day of Study | | | | Std Error |
|---|---|---|---|---|---|
| | 21 | 22 | 23 | 24 | |
| T01 saline IM | 38.1 | 38.3 | 38.2 | 38.2 | 0.10 |
| T02 saline SC | 38.5 | 38.5 | 38.2 | 38.2 | 0.10 |
| T03 p68 SC | 38.0 | 38.3 | 38.1 | 38.1 | 0.08 |
| T04 p68 IM | 38.1 | 38.4 | 38.4 | 38.4 | 0.08 |

[a]Second vaccination administered on Day 21.

No significant difference was noted between any groups on any day following the first vaccination. A significant difference was noted between saline vaccinated dogs and all p68 vaccinated dogs (p=0.0053 for T01T02 v T03T04) on Day 21. A significant difference (p=0.0124) between p68 SC and IM vaccinates was demonstrated on Day 24.

Injection Site Reactions

Injection site reactions are summarized in Tables 12 and 13. Due to technical oversight, no injection site observations were conducted at the 14-day observation following the second vaccination (Day 35).

Measurable site reactions were observed in T03 (p68 SC) and were minimal in size. A small injection site reaction was noted in one dog in T04 (p68 IM) on Day 3 but the minimal impact of the measurement is not reflected in the overall mean for the group.

TABLE 12

Least squares mean (cubic cm) of injection site reactions in dogs following saline or p68 (15 μg/dose) *Bordetella* vaccination (post first vaccination[a])

| Treatment[b] | Mean Size (cubic cm) of Injection Site Reactions Day of Study | | | | | | | |
|---|---|---|---|---|---|---|---|---|
| | 1 | 2 | 3 | 4 | 5 | 6 | 7 | 14 |
| T01 saline IM | 0.0 | 0.0 | 0.0 | 0.0 | 0.0 | 0.0 | 0.0 | 0.0 |
| T02 saline SC | 0.0 | 0.0 | 0.0 | 0.0 | 0.0 | 0.0 | 0.0 | 0.0 |
| T03 p68 SC | 7.4 | 4.3 | 6.8 | 3.4 | 2.5 | 2.6 | 1.9 | 0.1 |
| T04 p68 IM | 0.0 | 0.0 | 0.0[c] | 0.0 | 0.0 | 0.0 | 0.0 | 0.0 |

[a]First vaccination administered on Day 0
[b]standard error for T01 = 0.80, T02 = 0.84, T03 = 0.70, and T04 = 0.70
[c]one dog had a small site reaction (0.5 cm²) but due to rounding, the minimal impact of value is not reflected in overall mean.

TABLE 13

Least squares mean (cubic cm) of injection site reactions in dogs following saline or p68 (15 μg/dose) *Bordetella* vaccination (post second vaccination[a])

| Treatment[b] | Mean Size (cubic cm) of Injection Site Reactions Day of Study | | | | | | |
|---|---|---|---|---|---|---|---|
| | 22 | 23 | 24 | 25 | 26 | 27 | 28 |
| T01 saline IM | 0.0 | 0.0 | 0.0 | 0.0 | 0.0 | 0.0 | 0.0 |
| T02 saline SC | 0.0 | 0.0 | 0.0 | 0.0 | 0.0 | 0.0 | 0.0 |
| T03 p68 SC | 8.6 | 9.2 | 9.5 | 7.3 | 5.2 | 4.7 | 5.1 |
| T04 p68 IM | 0.0 | 0.0 | 0.0 | 0.0 | 0.0 | 0.0 | 0.0 |

[a]Second vaccination administered on Day 21
[b]standard error for T01 = 1.12, T02 = 1.19, T03 = 0.92, and T06 = 0.92

Significant differences in injection sites measurements are summarized in Table 14. A significant difference in injection site measurements between T02 (saline SC) versus T03 (p68 15 μg SC) was noted for six days following the first vaccination. By Day 7 and again on Day 14 (the two week re-evaluation observation), no significant differences were noted between any treatment group.

A significant difference in injection site measurements between T02 (saline SC) versus T03 (p68 15 μg SC) was noted for seven days following the second vaccination.

TABLE 14

Significance values for a priori contrasts among least squares mean of injection site reaction measurements.

| Day of Study | Contrasts (treatment v. treatment) | p-value |
|---|---|---|
| 1 | T02 v T03 | 0.0001 |
| | T03 v T04 | 0.0001 |
| | T01T02 v T03T04 | 0.0001 |

TABLE 14-continued

Significance values for a priori contrasts among least squares mean of injection site reaction measurements.

| Day of Study | Contrasts (treatment v. treatment) | p-value |
|---|---|---|
| 2 | T02 v T03 | 0.0007 |
| | T03 v T04 | 0.0008 |
| | T01T02 v T03T04 | 0.0101 |
| 3 | T02 v T03 | 0.0001 |
| | T03 v T04 | 0.0001 |
| | T01T02 v T03T04 | 0.0002 |
| 4 | T02 v T03 | 0.0044 |
| | T03 v T04 | 0.0042 |
| | T01T02 v T03T04 | 0.0339 |
| 5 | T02 v T03 | 0.0313 |
| | T03 v T04 | 0.0253 |
| 22 | T02 v T03 | 0.0001 |
| | T03 v T04 | 0.0001 |
| | T01T02 v T03T04 | 0.0002 |
| 23 | T02 v T03 | 0.0001 |
| | T03 v T04 | 0.0001 |
| | T01T02 v T03T04 | 0.0001 |
| 24 | T02 v T03 | 0.0001 |
| | T03 v T04 | 0.0001 |
| | T01T02 v T03T04 | 0.0001 |
| 25 | T02 v T03 | 0.0001 |
| | T03 v T04 | 0.0001 |
| | T01T02 v T03T04 | 0.0013 |
| 26 | T02 v T03 | 0.0013 |
| | T03 v T04 | 0.0007 |
| | T01T02 v T03T04 | 0.0172 |
| 27 | T02 v T03 | 0.0035 |
| | T03 v T04 | 0.0019 |
| | T01T02 v T03T04 | 0.0313 |
| 28 | T02 v T03 | 0.0017 |
| | T03 v T04 | 0.0010 |
| | T01T02 v T03T04 | 0.0200 |

Only significant (P < 0.05) contrasts are presented.

p68 ELISA Titers p68 ELISA data are summarized in Table 15 and FIG. 1. Due to the considerable titer response to p68 in the vaccinated dogs, various titration minimums were used at different timepoints in the study. Titrations for Days 0 and 21 were started at 50. For Days 35, 45 and 59, titrations were begun at 200. Any value reported as "less than" was divided by 2 prior to analysis. The incremental rise observed in p68 ELISA values for control groups (T01 and T02) during the course of the study is due to these minimum titration values. Agglutination titers remained<4.

All p68 vaccinated animals demonstrated at least a fourfold increase in titers from the first day of vaccination to the day of challenge (Day 0 vs. Day 45) when compared to placebo vaccinated animals.

TABLE 15

Geometric mean and standard errors of p68 (15 μg/dose) ELISA endpoint titers[a] in dogs following saline or p68 (15 μg/dose) vaccination and following *B. bronchiseptica* aerosol challenge.

| | Day of Study[b] | | | | | | | | | |
|---|---|---|---|---|---|---|---|---|---|---|
| Treatment | 0 | Std error | 21 | Std error | 35 | Std error | 45 | Std error | 59 | Std error |
| T01 saline IM | 25.0 | 4.78 | 25.0 | 4.78 | 125.4 | 23.96 | 100.0 | 18.14 | 130.0 | 32.24 |
| T02 saline SC | 25.0 | 5.06 | 25.0 | 5.06 | 113.5 | 23.00 | 100.0 | 19.39 | 100.0 | 26.50 |
| T03 p68 SC | 25.0 | 3.93 | 189.5 | 29.77 | 10688.7 | 1679.20 | 4555.1 | 603.43 | 8796.0 | 1592.43 |
| T04 p68 IM | 25.0 | 3.93 | 121.4 | 19.08 | 11023.7 | 1731.85 | 4419.2 | 585.44 | 13718.1 | 2483.54 |

[a]Titrations for Days 0 and 21 were started at 50. Titrations for Days 35, 45 and 59 were stared at 200. Any value reported as "less than" was divided by 2 prior to analysis.
[b]First vaccination occurred on Day 0; Second vaccination occurred on Day 21 and challenge was administered on Day 45.

Significant differences for least squares mean of post vaccination and post challenge ELISA titers are listed in Table 16. No significant difference was noted between the p68 SC and p68 IM vaccinated animals after vaccination was complete.

TABLE 16

Significance values for a priori contrasts among least square mean of post vaccination and post challenge p68 ELISA endpoint titers.

| Day of study | Contrast | p-value |
|---|---|---|
| 21 | T01 v T04 | 0.0001 |
|  | T02 v T03 | 0.0001 |
|  | T03 v T04 | 0.0491 |
| 35 | T01 v T04 | 0.0001 |
|  | T02 v T03 | 0.0001 |
| 45 | T01 v T04 | 0.0001 |
|  | T02 v T03 | 0.0001 |
| 59 | T01 v T04 | 0.0001 |
|  | T02 v T03 | 0.0001 |

Only significant ($P < 0.05$) contrasts are presented.

Serum Amyloid A Titers

SAA values were determined on Days 0, 1, 3, 5, 7 and 9 following challenge. Serum Amyloid A values are presented in Table 17 and represented in FIG. 2.

TABLE 17

Geometric mean and standard errors of Serum Amyloid A titers in saline and p68 (15 µg/dose) *Bordetella* vaccinated dogs following aerosol challenge with *Bordetella bronchiseptica*

| | Geometric Mean and Standard Errors of Serum Amyloid A Day of Study[a] | | | | | | | | | | | |
|---|---|---|---|---|---|---|---|---|---|---|---|---|
| | 45 | | 46 | | 48 | | 50 | | 52 | | 54 | |
| TRT | Mean | Std. error | Mean | Std. error | Mean | Std. Error | Mean | Std. error | Mean | Std. error | Mean | Std. error |
| T01 | 0.1 | 0.02 | 277.3 | 125.30 | 82.4 | 42.17 | 69.8 | 28.60 | 6.0 | 2.24 | 1.2 | 0.33 |
| T02 | 0.4 | 0.06 | 384.5 | 185.63 | 128.9 | 70.46 | 215.9 | 94.56 | 28.0 | 11.23 | 3.7 | 1.11 |
| T03 | 0.5 | 0.05 | 31.7 | 10.51 | 6.0 | 2.25 | 2.3 | 0.68 | 0.8 | 0.23 | 1.3 | 0.27 |
| T04 | 0.3 | 0.04 | 50.0 | 16.58 | 8.6 | 3.22 | 5.0 | 1.50 | 2.4 | 0.65 | 0.7 | 0.14 |

[a] Challenge administered on Day 45

Significant differences in SAA titers are summarized in Table 18. Saline controls demonstrated higher SAA titers than vaccinated dogs on Days 1, 3 and 5 following challenge. Saline SC controls continued to demonstrate significantly higher SAA titers when compared to vaccinated SC dogs on Day 7 and 9 following challenge.

TABLE 18

Significance values for a priori contrasts among least square mean of Serum Amyloid A titers postchallenge.

| Day of study | Contrast (treatment v treatment) | p-value |
|---|---|---|
| 46 | T01 v T04 | 0.0025 |
|  | T02 v T03 | 0.0001 |
| 48 | T01 v T04 | 0.0007 |
|  | T02 v T03 | 0.0001 |
| 50 | T01 v T04 | 0.0001 |
|  | T02 v T03 | 0.0001 |

TABLE 18-continued

Significance values for a priori contrasts among least square mean of Serum Amyloid A titers postchallenge.

| Day of study | Contrast (treatment v treatment) | p-value |
|---|---|---|
| 52 | T01 v T02 | 0.0093 |
|  | T02 v T03 | 0.0001 |
| 54 | T02 v T03 | 0.0493 |

Only significant ($P < 0.05$) contrasts are presented.

Coughing Observations

Aerosol challenge for all treatment groups occurred 24 days following the second vaccination (Day 45). Coughing observations were examined using two methods—disease status based on two consecutive days coughing (presented in Table 19) and percentage of days coughing (presented in Tables 20 and 21). When dogs were evaluated using criteria of two consecutive days coughing, 80% of the p68 vaccinated dogs (SC and IM) coughed at least two consecutive days whereas the Saline SC and Saline IM vaccinated dogs coughed 100% and 87.5%, respectively. When dogs were evaluated using percentage of days observed coughing, p68 SC and IM vaccinated dogs coughed 38.72% and 41.05% of the days observed, respectively. Saline SC and Saline IM vaccinated dogs coughed 69.04% and 62.66%, respectively.

TABLE 19

Summary of disease status in saline and p68 (15 µg/dose) *Bordetella* vaccinated dogs based on two consecutive days coughing following aerosol challenge with *Bordetella bronchiseptica*

| Treatment Number | # of Dogs | Percent Dogs with Two Consecutive Days Coughing |
|---|---|---|
| T01 Saline IM | 8 | 87.5 |
| T02 Saline SC | 7 | 100.0 |
| T03 p68 15 µg/dose SC | 15 | 80.0 |
| T04 p68 15 µg/dose IM | 15 | 80.0 |

No significant difference was demonstrated between saline vaccinated and p68 vaccinated dogs when disease status was based on two consecutive days coughing.

TABLE 20

Mean percentage of days coughing in saline and p68 (15 μg/dose) Bordetella vaccinated dogs following aerosol challenge with Bordetella bronchiseptica

| Treatment | Number of Dogs | Mean | Std Error |
|---|---|---|---|
| T01 Saline IM | 8 | 62.66% | 8.67 |
| T02 Saline SC | 7 | 69.04% | 8.86 |
| T03 p68 15 μg SC | 15 | 38.72% | 6.38 |
| T04 p68 15 μg IM | 15 | 41.05% | 6.44 |

A significant difference (p=0.0112) was demonstrated between T02 (saline SC) and T03 (p68 15 μg SC). No significant difference was demonstrated between T01 (saline IM) and T04 (p68 15 μg IM).

TABLE 21

Mean percentage of days coughing by treatment in saline and p68 (15 μg/dose) Bordetella vaccinated dogs following aerosol challenge with Bordetella bronchiseptica

| Parameter | Estimate | Std error |
|---|---|---|
| Saline mean (T01 & T02) | 65.89% | 1.10 |
| 15 μg/dose mean (T03 & T04) | 39.88% | 4.34 |

A significant difference (p=0.0022) was demonstrated between the saline controls and p68-vaccinated dogs.

Discussion

The study was designed to demonstrate the safety and efficacy of a p68 Bordetella 15 μg/dose vaccine in dogs.

Safety was examined using injection site and rectal temperature observations. Analysis of injection site reaction measurements demonstrated a negligible reaction in the IM vaccinated group and minimal reactions in SC vaccinated group. Reactions that were observed tended to be small, generally decreasing in size during the observation periods. The size of these reactions would most likely go unnoticed on unshaven dogs. Although a significant difference was observed between saline and vaccinated on Day 21 and between IM and SC vaccinates on Day 24, rectal temperatures were clinically unremarkable and were within normal limits for all dogs in all groups.

Efficacy was examined using observations of measurement of p68 ELISA endpoint titers and coughing. Regardless of the route of administration, a good p68 antibody response was demonstrated in p68-vaccinated groups by Day 35. A good anamnestic response was observed in vaccinates post challenge. Although higher antibody responses have traditionally been obtained with the more vascular and less fatty IM route as compared to the SC route, the difference between p68 SC and IM vaccinates was not significant through the course of the study.

Examination of the SAA response in vaccinated and unvaccinated p68 Bordetella dogs following challenge indicated a much smaller rise in the SAA values in vaccinated animals groups especially on days 1, 3 and 5 days post-challenge.

Conclusions

In this study, efficacy a 15 μg/dose p68 canine Bordetella vaccine was examined using a canine challenge model 24 days after vaccination. The vaccine was safe as demonstrated by normal rectal temperatures, minimal injection site reactions and efficacy was demonstrated in combined IM and SC groups. Comparison of SAA values demonstrated a significant difference between saline and p68 vaccinated dogs on Days 1, 3 and 5 following aerosol challenge.

EXAMPLE 3

Six Month Duration of Immunity Study of Canine Bordetella p68 Vaccine

Animals

Ninety male and female mixed breed dogs were purchased and the majority of puppies were 9 weeks (±1 week) on the day of first vaccination.

A MLV parvovirus vaccine was administered to dogs upon arrival at the study site. To be eligible for the study, animals were determined to be negative to B. bronchiseptica by tracheal swab and agglutination titer. No vaccines, other than the experimental products, were administered during the study.

Dogs were kept in an isolation facility necessary to prevent exposure to B. bronchiseptica and canine pathogens prior to challenge. After aerosol challenge with B. bronchiseptica, isolation procedures were continued to prevent exposure to other canine pathogens.

Vaccines

Sterile saline was used as a placebo vaccine in treatment groups T01 and T02. Canine recombinant p68 Bordetella Bronchiseptica Vaccine was used in treatment groups T03 and T04. The structural gene of the p68 antigen was cloned in Escherichia coli and expression of the gene was regulated by a temperature sensitive promoter. The cells were lysed and the inclusion bodies were separated by centrifugation. The recombinant p68 in the inclusion bodies was solubilized by SDS treatment. Separately, the 15 μg p68 and 60 μg p68 were combined with 50 μg of Quil A and 50 μg of cholesterol per mL in sterile Lepto saline as the diluent. The combined components were mixed at 4° C. for 24 hours and passed three times through a microfluidizer. Each one mL dose contained 2.7 μl of ethanol and 0.0001% thimerosal. p68 concentrations in the experimental vaccines were measured by p68 ELISA. All assays were done in replicates of five (5). All vaccines were used within 6 months of assembly.

Challenge Inoculum

Bordet-Genou agar plates were plated with Bordetella bronchiseptica—Bihr Cat strain and incubated for 48 hours at 37.5+/−2.5° C. Virulent phase I colonies were selected and streaked on Bordet-Genou agar and incubated for 24 hours at 37.5+/−2.5° C. After incubation, Bordetella saline was used to wash colonies from agar and the cells diluted to an optical density of 0.80 at 600 nm. A cell count was performed pre and post challenge for confirmation of the nephelometer reading. Challenge target concentration was approximately $1 \times 10^9$ CFU. For Group I, the prechallenge concentration count was $1.94 \times 10^9$ and the post challenge concentration count was $1.43 \times 10^9$. For Group II, the prechallenge concentration count was $2.55 \times 10^9$ and the post challenge concentration count was $2.13 \times 10^9$.

Study Design

SUMMARY TABLE

| Treatment Group | Treatment | Route | Number of Animals Day of First Vaccination | | Total Number of Animals |
|---|---|---|---|---|---|
| | | | Day 0 (Group I) | Day 20 (Group II) | |
| T01 | Saline Control | Subcutaneous | 8 | 7 | 15 |
| T02 | Saline Control | Intramuscular | 8 | 7 | 15 |

SUMMARY TABLE-continued

| Treatment Group | Treatment | Route | Number of Animals Day of First Vaccination | | Total Number of Animals |
|---|---|---|---|---|---|
| | | | Day 0 (Group I) | Day 20 (Group II) | |
| T03 | p68 60 µg/dose | Subcutaneous | 8 | 7 | 15 |
| T04 | p68 60 µg/dose | Intramuscular | 8 | 7 | 15 |
| T05 | p68 15 µg/dose | Subcutaneous | 8 | 7 | 15 |
| T06 | p68 15 µg/dose | Intramuscular | 8 | 7 | 15 |

The study was conducted in two phases or groups consisting of 48 dogs in Group I and 42 dogs in Group II. Vaccination #1 occurred on Day 0 for the each Group. Vaccination #2 occurred 20 days later. Events in Group I were offset from the events in Group II by approximately 15 days. Dogs were aerosol challenged with *B. bronchiseptica* 181 days after the last vaccination.

Randomization/Blinding

Animals were randomly assigned to treatments and rooms according to a complete randomized design.

For the time period from vaccination #1 to day of challenge within each study group, animals were randomly assigned to treatments and rooms (3 to 5 dogs per room) using a randomization plan.

On the day of challenge, the previously treated animals were randomized to challenge rooms within study group using a generalized block design.

Qualified individuals, unaware of the assigned treatment groups, conducted microbiological and serological assays and assessments of coughing and injection sites.

Data Analysis

Post vaccination response variables consisted of injection site data, rectal temperatures and p68 ELISA titers. Injection site data was summarized as follows: 1) number of animals having a measurable reaction by treatment and day of study, 2) number of animal time points having a measurable reaction by treatment, 3) number of animals having a measurable reaction at any time point by treatment, 4) duration of a measurable reaction for each animal.

Separately for first and second vaccinations, injection site volume (cubic cm), rectal temperatures and natural log transformed p68 ELISA titer data was analyzed using a general linear mixed model.

A priori linear contrasts of the treatment by observation time point least squares mean was constructed to test treatment group differences at each observation time point and to compare time points within each treatment. The specific comparisons of interest were T01 vs. T03, T01 vs. T05, T03 vs. T05, T02 vs. T04, T02 vs. T06, and T04 vs. T06. If the time point-by-treatment-by-study group interaction term was significant at $P<0.05$, contrasts among treatment groups at each time point and among time points within treatment groups was within each study group, otherwise these contrasts were based on the time point-by-treatment interaction effect least squares mean. The 5% level of significance was used for all comparisons.

Post challenge response variables consisted of p68 ELISA titers, Serum Amyloid A titers and daily coughing observations. Post challenge p68 ELISA titers were analyzed as previously described. For Serum Amyloid A (SAA) titer data post challenge, the natural log transformation was applied to titer values prior to analysis using a general linear mixed model.

The analysis of coughing was amended to reflect USDA requirements. For each dog, the percentage of observation periods during which coughing was observed was calculated. Prior to analysis, the percentage was transformed using the arcsin square root transformation. A general linear mixed model was used for analysis of coughing.

Least squares mean from this analysis were back-transformed to percentages and the percent reduction in coughing was calculated as:

Percent Reduction=100×(control group mean—treatment group mean)(control group mean)

A priori linear contrasts of the treatment least squares mean was constructed to test treatment group differences. The specific comparisons of interest were T01 vs. T03, T01 vs. T05, T03 vs. T05, T02 vs. T04, T02 vs. T06, and T04 vs. T06. If the treatment-by-study group interaction term was significant at $P<0.05$, contrasts among treatment groups was within each study group otherwise contrasts among treatment groups were based on the treatment main effect least squares mean. The 5% level of significance was used for all comparisons.

Study Procedure

Detailed Animal Procedures

Prior to arrival on study premises and prior to the first vaccination, puppies were tracheal swabbed for *B. bronchiseptica* culture and blood was collected for agglutination titers. All animals were negative by tracheal swab and serologically negative to *Bordetella* and deemed eligible for the study. Forty-eight puppies were randomly assigned to one of six treatment groups for Group I. The procedure was repeated using forty-two dogs for Group II. Animals were acclimated to the study site for at least five days.

Groups and treatments are detailed in Section 7.4.A. Due to facility constraints and to enhance the accuracy of coughing observations following challenge, the vaccination and the respective challenge periods were staggered by 15 days to generate the two dog groups. Day 0 refers to the day of vaccination #1 for both Group I and II. Vaccination #2 occurred 20 days later. Treatments T01, T03, and T05 were administered via the subcutaneous route. Treatments T02, T04, and T06 were administered via the intramuscular route. Subcutaneous injections were administered in the dorsolateral aspect of the neck. For vaccination #1, the right side of the neck was used and for vaccination #2, the left side of the neck was used. Intramuscular injections were administered in the right and left semimembranosus muscle for vaccination #1 and vaccination #2, respectively. All injection sites were measured three dimensionally for seven days following each vaccination with a follow-up measurement done 14 days following vaccination. Rectal temperatures were monitored on the day of vaccination (prior to vaccination) and for three days following each vaccination. Blood was collected prior to each vaccination (on Day-1 and Day 19) and on Day 50 for p68 ELISA titer determination.

Each month, all dogs were tracheal swabbed for *B. bronchiseptica* culture under sedation to confirm *B. bronchiseptica* negative status. Blood was also collected for agglutination and ELISA titers. The procedure was repeated 7 days prior to challenge for each group. Evidence of a positive tracheal swab culture or a rising agglutination titer excluded the animal from the study.

Challenge was administered to dogs 181 days after vaccination #2. Sedated dogs were challenged using a disposable nose cone, which was fitted snuggly over the muzzle of the sedated dog. The nose cone was attached to a nebulizer which was attached to a vacuum pressure pump set at 5.5 to 6.0 psi. One mL of challenge material was placed in the nebulizer and the aerosolized challenge material was administered to each dog for 4 minutes.

Post challenge coughing observations were amended prior to challenge to comply with USDA recommendations. After challenge, each group of dogs was observed between the third and tenth day following challenge, for a total of 8 days. Animals were observed twice daily for coughing for approximately 45 minutes at each observation period. The interval between observation periods was approximately 12 hours. Personnel unaware of the assigned treatment groups recorded coughing observations.

Blood Collection

Blood for agglutination titers was collected prior to first vaccination, monthly and prior to challenge for each group.

Blood for anti-p68 ELISA evaluation was collected the day before vaccination #1 and #2, on Day 50 and at approximately 30 day intervals thereafter for each group. Blood was also collected the day of challenge and on the final day of post challenge observation.

Blood for Serum Amyloid A (SAA) assay was collected on the day of challenge (prior to challenge) and on 1, 3, 5, 7, and 9 days post challenge for each group.

Tests Performed on Samples

Tracheal swabs were evaluated for the presence of *B. bronchiseptica* by culture. Each tracheal swab was streaked onto a *Bordetella* Selective Agar plate. Positive and negative controls are included. The plates were incubated at 37.5±2.5° C. for 48±4 hours. The resulting colonies on each plate were compared to the positive control and any colony which appeared identical to the positive control was further tested to confirm the presence of *B. bronchiseptica*. Confirmational testing included the use of TSI, Citrate and Urea Agar and Nitrate Red media.

Sera were evaluated for agglutination titers, p68 ELISA analysis or SAA analysis using the following methods:

Agglutination titers—Sera were serially diluted in microtiter plates using *Bordetella* saline. Positive and negative controls were included on each plate. *B. bronchiseptica* Strain 87 (grown on Bordet Genou agar, harvested, inactivated and diluted to 20% T at 630 nm) was used as the agglutinating antigen and was added to each well. Plates were shaken and incubated at 35±2° C. for 2 hours. Plates were read after a second incubation at room temperature for 22 hours. The endpoint titer was determined using the last well to show 50% agglutination.

p68 ELISA titers—The recombinant p68 antigen was captured on a 96 well microtiter plate coated with a polyclonal antiserum specific to the *Bordetella* p68 antigen. Serial two fold dilutions of the canine serum were added to the plate and incubated. Positive and negative controls at a 1:1000 dilution were included on each plate. A peroxidase labeled affinity purified goat anti-dog IgG indicator conjugate was used to detect antibodies specific for the rp68 antigen. A chromogenic substrate ABTS was then added and the plate read when the positive control wells had an O.D. of 1.2±0.2. The titer of a given sample was calculated as the reciprocal of the last dilution with an optical density greater than the mean of the negative control serum dilution plus five standard deviations.

SAA titers—The canine Serum Amyloid A was captured on a 96 well microtiter plate coated with a monoclonal anti-canine SAA antibody. Diluted samples of the canine serum were added to the plate and incubated. A reference standard was added to obtain a standard curve from 0.31 ng/ml to 20 ng/ml. A biotin labeled anti-canine antibody conjugate was added. Following the incubation of the biotin labeled anti-canine antibody, a peroxidase conjugated streptavidin was added. A chromogenic substrate TMB was added and the plate was read after 30 minutes. The concentration of Serum Amyloid A was determined by comparison the sample to the standard curve and multiplication by the appropriate dilution factor.

Results

Unless otherwise noted, results are the combined data from Group I and II.

Tracheal Swab Culture and Agglutination Titers

Positive tracheal swab cultures and/or rising agglutination titers were demonstrated in eleven dogs during the course of the study. These dogs and any dog housed with the positive dogs were removed from the study, resulting in a loss of 20 dogs. The number of dogs removed from each group was: T01-4 dogs, T02-2 dogs, T03-3 dogs, T04-1 dog, T05-5 dogs, T06-5 dogs.

Injection Site Observations

Injection site reactions are summarized in Tables 22-25. Injection site information was not collected for Dog 81595 on Day 21 for Group I due to technical oversight. The protocol was amended so that injection site reaction data was not collected for dogs in Group II on Day 22 therefore, summary of data from Day 22 contains only information from the eight dogs per treatment group in Group I. Injection site reactions were not observed for any dog receiving an IM treatment. Injection site measurements were minimal for both SC vaccinated treatment groups (T03 and T05).

TABLE 22

Least squares mean (cubic cm) of injection site reactions in dogs following saline or p68 *Bordetella* vaccination (post first vaccination[a])

| | Mean Size (cubic cm)[b] Day of Study | | | | | | | |
|---|---|---|---|---|---|---|---|---|
| Treatment | 1 | 2 | 3 | 4 | 5 | 6 | 7 | 14 |
| T01 saline SC | 0 | 0 | 0 | 0 | 0 | 0 | 0 | 0 |
| T02 saline IM | 0 | 0 | 0 | 0 | 0 | 0 | 0 | 0 |
| T03 60 µg SC | 5.8 | 6.4 | 7.3 | 6.3 | 5.0 | 4.9 | 2.7 | 0 |
| T04 60 µg IM | 0 | 0 | 0 | 0 | 0. | 0 | 0 | 0 |
| T05 15 µg SC | 4.4 | 4.6 | 3.1 | 2.1 | 1.2 | 0.9 | 0.7 | 0 |
| T06 15 µg IM | 0 | 0 | 0 | 0 | 0 | 0 | 0 | 0 |

[a]Vaccination #1 administered on Day 0
[b]standard error for all means = 0.64

TABLE 23

Least squares mean (cubic cm) of injection site reactions in dogs following saline or p68 *Bordetella* vaccination (post second vaccination[a])

| | Mean Size (cubic cm) Day of Study | | | | | | | |
|---|---|---|---|---|---|---|---|---|
| Treatment | 21[b] | 22[c] | 23[b] | 24[b] | 25[b] | 26[b] | 27[b] | 34[b] |
| T01 saline SC | 0 | 0 | 0 | 0 | 0 | 0 | 0 | 0 |
| T02 saline IM | 0 | 0 | 0 | 0 | 0 | 0 | 0 | 0 |
| T03 60 µg SC | 5.0 | 3.2 | 4.2 | 5.8 | 5.9 | 5.8 | 4.3 | 0.1 |
| T04 60 µg IM | 0 | 0 | 0 | 0 | 0 | 0 | 0 | 0 |
| T05 15 µg SC | 3.7 | 2.4 | 2.2 | 2.6 | 2.1 | 2.0 | 1.6 | 0 |
| T06 15 µg IM | 0[d] | 0 | 0 | 0 | 0 | 0 | 0 | 0 |

[a]Vaccination #2 administered on Day 20
[b]standard error for means on this day = 0.55
[c]standard error for means on this day = 0.70
[d]standard error for T06 on Day 21 = 0.57

TABLE 24

Percent of dogs having a measurable injection site reaction following vaccination with saline or p68 Bordetella (post first vaccination[a])

| | | Percent Measurable Reaction | | | | | | | |
|---|---|---|---|---|---|---|---|---|---|
| Treatment | n | 1 | 2 | 3 | 4 | 5 | 6 | 7 | 14 |
| T01 saline SC | 15 | 0 | 0 | 0 | 0 | 0 | 0 | 0 | 0 |
| T02 saline IM | 15 | 0 | 0 | 0 | 0 | 0 | 0 | 0 | 0 |
| T03 60 µg SC | 15 | 66.7 | 73.3 | 73.3 | 73.3 | 73.3 | 73.3 | 66.7 | 0 |
| T04 60 µg IM | 15 | 0 | 0 | 0 | 0 | 0 | 0 | 0 | 0 |
| T05 15 µg SC | 15 | 73.3 | 73.3 | 60.0 | 60.0 | 53.3 | 46.7 | 46.7 | 0 |
| T06 15 µg IM | 15 | 0 | 0 | 0 | 0 | 0 | 0 | 0 | 0 |

[a]Vaccination #1 administered on Day 0

TABLE 25

Percent of dogs having a measurable injection site reaction following vaccination with saline or p68 Bordetella (post second vaccination[a])

| | | Percent Measurable Reaction Day of Study | | | | | | | |
|---|---|---|---|---|---|---|---|---|---|
| Treatment | n | 21 | 22[b] | 23 | 24 | 25 | 26 | 27 | 34 |
| T01 saline SC | 15 | 0 | 0 | 0 | 0 | 0 | 0 | 0 | 0 |
| T02 saline IM | 15 | 0 | 0 | 0 | 0 | 0 | 0 | 0 | 0 |
| T03 60 µg SC | 15 | 80.0 | 50.0 | 66.7 | 66.7 | 80.0 | 80.0 | 80.0 | 6.7 |
| T04 60 µg IM | 15 | 0 | 0 | 0 | 0 | 0 | 0 | 0 | 0 |
| T05 15 µg SC | 15 | 73.3 | 50.0 | 73.3 | 73.3 | 73.3 | 73.3 | 66.7 | 0 |
| T06 15 µg IM | 15 | 0[c] | 0 | 0 | 0 | 0 | 0 | 0 | 0 |

[a]Vaccination #2 administered on Day 0
[b]n = 8 for Day 22
[c]n = 14 for T06 on Day 21

Significant differences in injection sites measurements are summarized in Table 26. A significant difference in injection sites measurements between T01 (saline SC) versus T03 (60 µg SC) was noted for seven days after the first vaccination. A significant difference between T01 (saline SC) and T05 (15 µg SC) was noted for only the first four days after the first vaccination. A significant difference was found between T03 (60 µg SC) and T05 (15 µg SC) on Days 3 through 7. By Day 14 (the two week re-evaluation observation), no difference was noted between any of the groups.

A significant difference (P=0.0138) in injection sites measurements between T01 (saline SC) versus T03 (60 µg SC) and T05 (15 µg SC) was noted for seven days after the second vaccination. A significant difference was found between T03 (60 µg SC) and T05 (15 µg SC) on Days 23 through 27. By Day 34 (the two week re-evaluation observation), no difference was noted between any of the groups

TABLE 26

Significance values for a priori contrasts among least squares mean of injection site reaction measurements.

| Day of Study | Contrasts (treatment v. treatment) | p-value |
|---|---|---|
| 1 | T01 v T03 | 0.0001 |
| | T01 v T05 | 0.0001 |
| 2 | T01 v T03 | 0.0001 |
| | T01 v T05 | 0.0001 |
| 3 | T01 v T03 | 0.0001 |
| | T01 v T05 | 0.0006 |
| | T03 v T05 | 0.0001 |
| 4 | T01 v.T03 | 0.0001 |
| | T01 v T05 | 0.0214 |
| | T03 v T05 | 0.0001 |
| 5 | T01 v T03 | 0.0001 |
| | T03 v T05 | 0.0001 |
| 6 | T01 v T03 | 0.0001 |
| | T03 v T05 | 0.0001 |
| 7 | T01 v T03 | 0.0031 |
| | T03 v T05 | 0.0258 |
| 21 | T01 v T03 | 0.0001 |
| | T01 v T05 | 0.0001 |
| 22 | T01 v T03 | 0.0010 |
| | T01 v T05 | 0.0166 |
| 23 | T01 v T03 | 0.0001 |
| | T01 v T05 | 0.0055 |
| | T03 v T05 | 0.0113 |
| 24 | T01 v T03 | 0.0001 |
| | T01 v T05 | 0.0008 |
| | T03 v T05 | 0.0001 |
| 25 | T01 v T03 | 0.0001 |
| | T01 v T05 | 0.0067 |
| | T03 v T05 | 0.0001 |
| 26 | T01 v T03 | 0.0001 |
| | T01 v T05 | 0.0104 |
| | T03 v T05 | 0.0001 |
| 27 | T01 v T03 | 0.0001 |
| | T01 v T05 | 0.0475 |
| | T03 v T05 | 0.0004 |

Only significant (P < 0.05) contrasts are presented.

Rectal Temperature

Rectal temperature measurements are summarized in Tables 27 and 28. The protocol was amended so that rectal temperature data were not collected for Group II dogs on Day 22, therefore, summary of data from Day 22 contains only information from the dogs per treatment group in Group I.

TABLE 27

Least squares mean of rectal temperature (° C.) in dogs following saline or p68 Bordetella vaccination (post first vaccination[a])

| | Rectal Temperature (° C.)[b] Day of Study | | | |
|---|---|---|---|---|
| Treatment | 0 | 1 | 2 | 3 |
| T01 saline SC | 38.5 | 38.4 | 38.3 | 38.2 |
| T02 saline IM | 38.4 | 38.2 | 38.4 | 38.2 |
| T03 60 µg SC | 38.4 | 38.5 | 38.2 | 38.3 |
| T04 60 µg IM | 38.4 | 38.5 | 38.4 | 38.4 |
| T05 15 µg SC | 38.5 | 38.5 | 38.2 | 38.2 |
| T06 15 µg IM | 38.5 | 38.4 | 38.3 | 38.4 |

[a]Vaccination #1 administered on Day 20.
[b]standard error = 0.09

TABLE 28

Least squares mean of rectal temperature (° C.) in dogs following saline or p68 *Bordetella* vaccination (post second vaccination[a])

| Treatment | Rectal Temperature (° C.) Day of Study | | | |
|---|---|---|---|---|
| | 20[b] | 21[b] | 22[c] | 23[b] |
| T01 saline SC | 38.6 | 38.5 | 38.3 | 38.4 |
| T02 saline IM | 38.6 | 38.6 | 38.3 | 38.4 |
| T03 60 μg SC | 38.7 | 38.6 | 38.6 | 38.4 |
| T04 60 μg IM | 38.8 | 38.7 | 38.5 | 38.5 |
| T05 15 μg SC | 38.6 | 38.6 | 38.5 | 38.4 |
| T06 15 μg IM | 38.7 | 38.7 | 38.4 | 38.5 |

[a]Vaccination #2 administered on Day 20
[b]standard error = 0.08
[c]standard error = 0.11

A significant difference was noted in rectal temperatures between T02 (saline IM) and T04 (60 μg IM) on Day 1 after the first vaccination. No significant difference was found in rectal temperatures between any group on any day after the second vaccination.

p68 ELISA Titers

Prechallenge p68 ELISA data are summarized in Table 29. Due to the response of Group I dogs in T06 on Day 19, an effect due to group was observed in the data analysis of p68 ELISA titers. The effect was small and did not influence other analyzed timepoints. Therefore, data from Group I and II are combined for reporting purposes.

Due to the considerable titer response to p68 in the vaccinated dogs, various titration minimums were used at different timepoints in the study. Titrations for Days-1 and 19 were started at 50. For days 50 through 195, titrations were begun at 200. Titrations for samples collected on Day 201 and 211 were started at 1000. Any value reported as "less than" was divided by 2 prior to analysis. The incremental rise observed in p68 ELISA values for control groups (T01 and T02) during the course of the study is due to these minimum titration values. Agglutination titers, except as previously noted, remained<4.

All placebo vaccinated dogs had p68 titers<200 on Day 50. All p68-vaccinated animals demonstrated at least a four-fold increase in titers after the second vaccination (Day 0 vs. Day 50) when compared to placebo vaccinated animals.

TABLE 29

Geometric mean and standard errors of p68 ELISA endpoint titers in dogs following p68 *Bordetella* vaccination on Day 0 and Day 20.

| Treatment | Day of Study | | | | | |
|---|---|---|---|---|---|---|
| | −1[a] | | 19[a] | | 50[b] | |
| | Mean | std. error | Mean | std. error | Mean | std error |
| T01 Saline SC | 31.4 | 5.06 | 30.5 | 4.92 | 100.0 | 16.14 |
| T02 Saline IM | 27.7 | 4.47 | 25.0 | 4.03 | 100.0 | 16.14 |
| T03 P68 60 ug SC | 29.8 | 4.80 | 507.6 | 81.92 | 10633.5 | 1715.94 |
| T04 P68 60 ug IM | 26.7 | 4.31 | 249.7 | 40.29 | 4722.2 | 762.02 |
| T05 P68 15 ug SC | 25.0 | 4.03 | 268.7 | 43.36 | 5622.8 | 907.35 |
| T06 P68 15 ug IM | 33.4 | 5.40 | 91.8 | 14.81 | 3528.9 | 569.46 |

[a]titrations for Days −1 and 19 were started at 50. Any value reported as "less than" was divided by 2 prior to analysis
[b]titrations for Day 50 were started at 200. Any value reported as "less than" was divided by 2 prior to analysis Significant differences for least squares mean of post vaccination ELISA titers are listed in Table 30. No significant difference in p68 ELISA titers was observed between SC controls and SC vaccinates or IM controls and IM vaccinates prior to vaccination (Day-1).

TABLE 30

Significance values for a priori contrasts among least square mean of post vaccination p68 ELISA endpoint titers.

| Day of study | Contrast | p-value |
|---|---|---|
| 19 | T01 v T03 | 0.0001 |
| | T01 v T05 | 0.0001 |
| | T02 v T04 | 0.0001 |
| | T02 v T06 | 0.0001 |
| | T03 v T05 | 0.0061 |
| | T04 v T06 | 0.0001 |
| 50 | T01 v T03 | 0.0001 |
| | T01 v T05 | 0.0001 |
| | T02 v T04 | 0.0001 |
| | T02 v T06 | 0.0001 |
| | T03 v T05 | 0.0059 |

Only significant (P < 0.05) contrasts are presented.

p68 ELISA titers measured during the course of the study are summarized in Table 31 and illustrated in FIG. 3.

During the course of the study, every attempt was made to coordinate activities between Groups I and II. For pivotal data collection time points (i.e. events surrounding vaccination and challenge), this was achieved. In three instances during the interim of the study, blood and tracheal swab collection varied by 1 or 2 days between groups. In order to summarize and report p68 ELISA data for this interim period, data from these days were combined. Therefore, Day 79 contains combined data from Day 79 (Group I) and Day 81 (Group II), Day 111 corresponds to Day 110 (Group II) and Day 111 (Group I) and Day 169 corresponds to Day 169 (Group II) and Day 170 (Group I). Per the protocol, data analysis was not performed on p68 ELISA data beyond Day 50.

TABLE 31

Summary of geometric mean of p68 ELISA endpoint titers in unvaccinated and p68 *Bordetella* vaccinated dogs following vaccination and aerosol challenge with *Bordetella bronchiseptica*

| | Geometric Mean of p68 ELISA Endpoint Titers[a] | | | | | | |
|---|---|---|---|---|---|---|---|
| | Day of Study[b,c] | | | | | | |
| Treatment | 79 | 110 | 140 | 169 | 195 | 201 | 211 |
| T01 Saline SC | 100.00 | 154.92 | 106.00 | 108.59 | 117.18 | 109.14 | 500.0 |
| T02 Saline IM | 112.85 | 145.33 | 130.61 | 115.51 | 113.43 | 112.37 | 500.0 |
| T03 60 µg SC | 3434.24 | 2884.97 | 1861.64 | 1895.56 | 3097.24 | 2408.61 | 81564.79 |
| T04 60 µg IM | 1508.60 | 1164.81 | 933.12 | 987.64 | 1142.01 | 1547.87 | 59940.47 |
| T05 15 µg SC | 1699.20 | 1511.80 | 1229.35 | 1312.62 | 2248.63 | 2244.47 | 29869.29 |
| T06 15 µg IM | 974.18 | 916.21 | 573.51 | 876.15 | 1505.01 | 1458.16 | 11503.28 |

[a] Titrations Days 50 through 195, were started at 200. Titrations for samples collected on Day 201 and 211 were started at 1000. Any value reported as "less than" was divided by 2 prior to analysis.
[b] Vaccination #1 and #2 was administered on Day 0 and 20, respectively. Challenge was administered on Day 201
[c] During the course of the study, every attempt was made to coordinate activities between Groups I and II. In three instances, blood collection for the Groups varied by 1 or 2 days. Data from these days were combined for data summary. Analysis was not done on p68 ELISA titer values collected beyond Day 50. Day 79 corresponds to Day 79 and 81, Day 110 corresponds to Day 110 and 111, Day 169 corresponds to Day 169 and 170.

Coughing Observations

Aerosol challenge for both groups occurred 181 days following the second vaccination. To comply with USDA recommendations, coughing criteria was amended to approximately 45-minute observations, approximately twelve hours apart on the third through eighth day following challenge. Coughing observations are summarized in Tables 32 and 33.

TABLE 32

Mean percentage of timepoints coughing in unvaccinated and p68 *Bordetella* vaccinated dogs following aerosol challenge with *Bordetella bronchiseptica*

| Treatment | Number of Dogs | Mean | Std Error |
|---|---|---|---|
| T01 Saline SC | 11 | 75.44% | 7.73 |
| T02 Saline IM | 13 | 80.50% | 6.64 |
| T03 p68 60 µg SC | 12 | 67.30% | 8.12 |
| T04 p68 60 µg IM | 14 | 71.81% | 7.32 |
| T05 p68 15 µg SC | 10 | 36.30% | 9.19 |
| T06 p68 15 µg IM | 10 | 39.55% | 9.18 |

TABLE 32

Mean percentage of timepoints coughing by treatment in unvaccinated and p68 *Bordetella* vaccinated dogs following aerosol challenge with *Bordetella bronchiseptica*

| Parameter | Estimate | Std error |
|---|---|---|
| Saline mean (T01 & T02) | 78.26% | 5.28 |
| 60 µg/dose mean (T03 & T04) | 69.58% | 5.68 |
| 15 µg/dose mean (T05 & T06) | 37.92% | 6.70 |

The percent reduction in coughing when compared to the saline control was 51.55% for the 15 µg/dose groups and 11.09% for the 60 µg/dose groups. Statistical significant differences are summarized in Table 34.

TABLE 34

Significance values for a priori contrasts among least squares mean for percentage of timepoints coughing

| Contrast | p-value |
|---|---|
| T01 v T05 | 0.0041 |
| T03 v T05 | 0.0199 |
| T02 v T06 | 0.0019 |
| T04 v T06 | 0.0119 |
| T01 & T02 v T05 & T06 | 0.0001 |

(Only significant (P < 0.05) contrasts are presented.)

Serum Amyloid A

SAA values were determined on Days 0, 1, 3, 5, 7 and 9 following challenge. Serum Amyloid A values are presented in Table 35 and represented in FIG. 4.

TABLE 35

Geometric mean and standard errors of Serum Amyloid A titers in unvaccinated and p68 *Bordetella* vaccinated dogs following aerosol challenge with *Bordetella bronchiseptica*

Geometric Mean and Standard Errors of Serum Amyloid A[a]
Day of Study

| | 201 | | 202 | | 204 | | 206 | | 208 | | 210 | |
|---|---|---|---|---|---|---|---|---|---|---|---|---|
| TX | Mean | Std. error | Mean | Std. error | Mean | Std. error | Mean | Std. error | Mean | Std. error | Mean | Std. error |
| T01 | 1.1 | 0.33 | 257.3 | 84.61 | 371.6 | 116.44 | 548.7 | 171.93 | 68.0 | 21.31 | 9.4 | 2.95 |
| T02 | 1.0 | 0.28 | 114.0 | 32.83 | 111.9 | 32.21 | 108.9 | 31.36 | 15.6 | 4.48 | 1.7 | 0.49 |
| T03 | 0.8 | 0.25 | 135.7 | 40.55 | 119.7 | 35.75 | 74.5 | 22.25 | 10.9 | 3.38 | 1.0 | 0.30 |
| T04 | 0.8 | 0.23 | 134.7 | 39.20 | 156.0 | 43.59 | 174.8 | 48.86 | 34.6 | 9.67 | 1.9 | 0.54 |
| T05 | 0.8 | 0.28 | 68.4 | 22.85 | 88.3 | 29.50 | 9.3 | 3.12 | 1.9 | 0.64 | 2.0 | 0.66 |
| T06 | 0.8 | 0.27 | 45.7 | 14.94 | 54.0 | 17.67 | 9.4 | 3.07 | 1.9 | 0.63 | 0.8 | 0.27 |

[a] challenge administered on Day 201.

Significant differences in SAA titers are summarized in Table 36.

TABLE 36

Significance values for a priori contrasts among least square mean of Serum Amyloid A titers postchallenge.

| Day of study | Contrast (treatment v treatment) | p-value |
|---|---|---|
| 202 | T01 v T05 | 0.0054 |
| | T02 v T06 | 0.0393 |
| | T04 v T06 | 0.0154 |
| 204 | T01 v T03 | 0.0097 |
| | T01 v T05 | 0.0020 |
| | T04 v T06 | 0.0154 |
| 206 | T01 v T03 | 0.0001 |
| | T01 v T05 | 0.0001 |
| | T02 v T06 | 0.0001 |
| | T03 v T05 | 0.0001 |
| | T04 v T06 | 0.0001 |
| 208 | T01 v T03 | 0.0001 |
| | T01 v T05 | 0.0001 |
| | T02 v T06 | 0.0001 |
| | T03 v T05 | 0.0023 |
| | T04 v T06 | 0.0001 |
| 210 | T01 v T03 | 0.0002 |
| | T01 v T05 | 0.0068 |

Only significant (P < 0.05) contrasts are presented.

Discussion

The study was designed to demonstrate the safety and six-month efficacy of a recombinant p68 *Bordetella* vaccine in dogs. Safety of both the 15 μg/dose and the 60 μg/dose vaccine was demonstrated. The efficacy and 6 month duration of immunity of the 15 μg/dose was well supported in the study.

Safety was examined using injection site and rectal temperature observations. Analysis of injection site reaction measurements demonstrated no reactions in the IM vaccinated groups and minimal reactions in both the 15 μg/dose and 60 μg/dose SC vaccinated groups. Reactions that were observed tended to be smaller in the 15 μg/dose SC vaccinated dogs. Such reactions that were seen were transient, generally resolving in 14 days or less. The size of these reactions would most likely go unnoticed on dogs where injection sites were not shaven. Rectal temperatures post vaccination were unremarkable and were within normal limits for all dogs in all groups.

Efficacy and duration of immunity were examined 181 days from vaccination using observations of coughing and measurement of p68 ELISA endpoint titers. The percentage of coughing in the saline controls (78.26%) indicated that the challenge administered to the study animals was acceptable. Percentage of time points coughing for the 15 μg/dose group (37.92%) demonstrated a 51.55% reduction in coughing when compared to the controls, satisfying the efficacy requirements mandated by the USDA. No protection was demonstrated in the 60 μg/dose group (69.58%) with dogs demonstrating minimal reduction in coughing when compared to the controls.

Although not statistically compared, it can be seen from Tables 29 and 31 that SC vaccinates tended to have higher antibody responses when compared to IM vaccinates. For the purposes of the discussion, further comments regarding the different dose groups combine the results of the IM and SC routes of administration.

Regardless of the route of administration, an excellent p68 antibody response was demonstrated in both vaccinated groups by Day 50 and was maintained by vaccinates throughout the course of the study. A good anamnestic response was observed in vaccinates post challenge.

Comparison of the p68 ELISA titers of the 15 μg/dose and 60 μg/dose during the course of the study indicated that the 60 μg/dose group showed a slightly higher titer response (FIG. 3). This response, although excellent, did not correlate with protection following aerosol challenge. p68 ELISA titer responses were variable in dogs removed from the study with positive tracheal swabs or rising agglutination titers. Three of the six controls removed from the study with positive tracheal swab cultures and/or rising agglutination titers maintained p68 ELISA titers of <200. There appears to be no correlation of p68 ELISA titers to the tracheal swab or agglutination titer status of dogs removed from the study.

Examination of the SAA response in vaccinated and unvaccinated p68 *Bordetella* dogs following challenge indicated a much smaller rise in the SAA values in the 15 μg/dose groups especially on days 5 and 7 post-challenge.

Conclusions

In this study, efficacy a 15 μg/dose and 60 μg/dose of a p68 canine *Bordetella* vaccine was examined using a canine challenge model 6 months after vaccination. Both vaccines were safe as demonstrated by normal rectal temperatures and minimal injection site reactions. Although both the 15 μg/dose and the 60 μg/dose vaccinated dogs showed good serological response to vaccination as measured by p68 ELISA titers, the response did not correlate with clinical protection in the 60 μg/dose vaccinated dogs. The 60 μg/dose vaccinated dogs demonstrated no significant difference in coughing when compared to unvaccinated controls. Good efficacy of the 15 μg/dose vaccine was demonstrated by a greater than 50% reduction in coughing when compared to controls. It is postulated that increased levels of SDS in the 60 μg/dose vaccine may result in the demonstrated difference in protection. Comparison of SAA values demonstrated a difference between vaccinates and controls.

EXAMPLE 4

Safety and Efficacy of VANGUARD® Plus 5/CV-L

VANGUARD® Plus 5/CV-L is a freeze-dried preparation of attenuated strains of CD virus, CAV-2, CPI virus, CPV, and inactivated whole cultures of *L. canicola* and *L. icterohaemorrhagiae*, plus a liquid preparation of inactivated CCV with an adjuvant. All viruses were propagated on established cell lines. The CPV fraction was attenuated by low passage on the canine cell line which gave it the immunogenic properties capable of overriding maternal antibody interference at the levels indicated in Table 38. The liquid component was used to rehydrate the freeze-dried component, which had been packaged with inert gas in place of vacuum.

Laboratory evaluation demonstrated that VANGUARD® Plus 5/CV-L immunized dogs against CD, ICH, CAV-2 and CPI respiratory disease, enteritis caused by CCV and CPV, and leptospirosis caused by *L. canicola* and *L. icterohaemorrhagiae*, and that no immunologic interference existed among the vaccine fractions. Extensive field safety trials showed it to be safe and essentially reaction-free in dogs as young as 6 weeks of age under normal usage conditions.

It was also demonstrated that CAV-2 vaccine cross-protects against ICH caused by CAV-1. Studies demonstrated that CAV-2 not only protects against ICH, but against CAV-2 respiratory disease as well. Canine adenovirus type 2 challenge virus was not recovered from CAV-2-vaccinated dogs in tests conducted.

The CPV fraction in VANGUARD® Plus 5/CV-L was subjected to comprehensive safety and efficacy testing. It was shown to be safe and essentially reaction-free in laboratory tests and in clinical trials under field conditions. Product safety was further demonstrated by a backpassage study which included oral administration of multiple doses of the vaccine strain to susceptible dogs, all of whom remained normal.

Research demonstrated that 3 doses of the vaccine with increased CPV virus titer can overcome serum neutralization (SN) titers associated with maternal antibody. Serum neutralization titers as low as 1:4 were shown by others to interfere with active immunization using conventional modified live vaccines. A clinical trial was conducted with fifty 6-week-old puppies [25 vaccinates (SN titer range –256) and 25 nonvaccinated controls (SN titer range 4-1024)] (Table 37). The group of vaccinates received 3 doses, with vaccinations administered 3 weeks apart beginning at 6 weeks of age. After 1 vaccination, 13/25 puppies exhibited a 4-fold or greater increase in CPV SN titer (seroconversion) (Table 38). Twelve of these 13 puppies had maternal SN titers<1:16 at the time of the first vaccination with the remaining puppy having an SN titer of 1:64. Another 9 puppies with initial SN titers between 1:16 and 1:256 seroconverted after the second vaccination. Their maternal antibody SN titers had declined to <1:64 at the time of the second vaccination. Similarly, the last 3 vaccinates, with initial SN titers of 1:128, seroconverted after the third vaccination, after their maternal antibody CPV titer dropped<1:64. Therefore, in this study, when 3 doses of vaccine were given beginning at 6 weeks of age, all 25 vaccinates, even those with the highest maternal antibody levels, became actively immunized (GM=1:1176; range of SN titers 128-4096). All 50 dogs were challenged 3 weeks after the third vaccination with a heterologous CPV challenge virus. Fourteen of 25 nonvaccinated control dogs died or showed illness severe enough to warrant euthanasia, while all 25 vaccinates remained essentially healthy. The high-titer, low-passage vaccine virus in VANGUARD® Plus 5/CV-L was therefore highly immunogenic and capable of stimulating active immunity in the presence of maternal antibodies.

The efficacy of the CCV fraction of VANGUARD® Plus 5/CV-L was demonstrated in an extensive vaccination challenge study. Sixteen 7- to 8-week-old puppies were vaccinated with VANGUARD® Plus 5/CV-L (vaccinates) and 17 with Vanguard® Plus 5/L (controls). All puppies received three 1-mL doses at 3-week intervals. Three weeks following the third vaccination, puppies were challenged with a virulent strain of CCV (CV-6). Clinical observations, temperatures, weights, and blood parameters were monitored for 21 days following infection. CCV vaccinates demonstrated a reduction in the occurrence of diarrhea and amount of virulent CCV shed when compared to controls. At 21 days postchallenge, fluorescent antibody staining for virulent CCV of small intestinal sections demonstrated a significant reduction (P) in detectable CCV antigen between CCV vaccinates and controls (Table 39).

TABLE 37

Initial Serum Neutralization (SN) Titers of Vaccinates and Controls

| SN Titers | # Vaccinates Included | # Controls Included |
|---|---|---|
| <1:2 | 3 | 0 |
| 1:4 | 4 | 3 |
| 1:8 | 1 | 3 |
| 1:16 | 4 | 1 |
| 1:32 | 2 | 5 |
| 1:64 | 3 | 1 |
| 1:128 | 6 | 3 |
| 1:256 | 2 | 3 |
| 1:512 | 0 | 5 |
| 1:1024 | 0 | 1 |

TABLE 38

Postvaccination Serum Neutralization (SN) Titers Geometric Mean (Range)[a]

| Groups | N | Prevaccination | Postvaccination 1 | Postvaccination 2 | Postvaccination 3[b] |
|---|---|---|---|---|---|
| All Vaccinated Dogs | 25 | 1:24 (<2-256) | 1:108 (8-1024) | 1:605 (8-4096) | 1:1176 (128->4096) |

TABLE 38-continued

Postvaccination Serum Neutralization (SN) Titers Geometric Mean (Range)[a]

| Groups | N | Prevaccination | Postvaccination 1 | 2 | 3[b] |
|---|---|---|---|---|---|
| Responders Post 1st Vaccination | 13 | 1:6 (<2-64) | 1:460 (64-1024) | 1:1745 (256-4096) | 1:1410 (256-4096) |
| Responders Post 2nd Vaccination | 9 | 1:87 (16-256) | 1:20 (8-64) | 1:376 (256-1024) | 1:1625 (256-4096) |
| Responders Post 3rd Vaccination | 3 | 1:128 (128) | 1:32 (16-64) | 1:25 (8-64) | 1:203 (128-256) |
| Nonvaccinated Control Dogs | 25 | 1:64 (4-1024) | 1:9 (<2-64) | 1:3 (<2-64) | <1:2 (<2-4) |

[a]Dogs were vaccinated at 6, 9, and 12 weeks of age.
[b]Pre-challenge SN titers

TABLE 39

Fluorescent Antibody Staining of Small Intestinal Sections 21 Days Following Challenge

| | | % Dogs Fluorescent Antibody Positive | |
|---|---|---|---|
| | Gut Section | Vaccinates | Controls |
| Duodenum | 1 | 0 | 89 |
| | 2 | 0 | 100 |
| | 3 | 0 | 100 |
| Jejunum | 4 | 0 | 89 |
| | 5 | 0 | 100 |
| | 6 | 12.5 | 56 |
| Ileum | 7 | 0 | 78 |
| | 8 | 12.5 | 78 |
| | 9 | 0 | 67 |
| | 10 | 12.5 | 56 |

Conclusions

In this study, an adjuvanted combination vaccine containing CD virus, CAV-2, CPI virus, CPV and inactivated whole cultures of L. canicola and L. icterohaemorrhagiae and CCV, was shown to be both safe and efficacious as a vaccine when used in puppies. The combination vaccine was also shown to overcome serum neutralization (SN) titers associated with maternal antibody.

EXAMPLE 5

Canine Bordetella Native p68 Immunogenicity Study

Animals

The study included two litters of SPF beagles and two litters of random source dogs. Dogs were assigned randomly to vaccinated or non-vaccinated groups. The study included a total of 10 vaccinated and 11 non-vaccinated dogs.

Preparation of Experimental Vaccine

B. bronchispetica (strain 110H) was harvested from a 48 hour Bordet-Gengou blood agar spread plates by washing the plate surface with 5 to 10 ml heat extraction buffer. Alternatively, cells grown in both culture (Charlotte Parker Defined Medium) were harvested by centrifugation discarding the supernatant fraction. Harvested cells were suspended in 25 mM Tris-HCL, pH 8.8 and incubated at 60° C. for 1 hour. Cell debris was separated from heat extract by centrifugation at 20,000×g at 4° C. for 30 minutes. Sodium azide (0.01%) was added to the heat extracted supernatant fraction which was then further clarified by microporous filtration.

Monoclonal antibody affinity resin was prepared by conjugation of monoclonal antibody (designated Bord 2-7) to CNBr-activated Sepharose 4B using standard procedures. Approximately 30.35 mg of monoclonal antibody was conjugated to 1 gram of affinity resin. Clarified heat extracted supernatant fraction (above) and Bord 2-7 affinity resin was combined at an approximate ratio of 1 liter extract to 20 ml resin.

Binding of the native p68 to the resin was facilitated by incubating the mixture at ambient temperature, with gentle shaking, overnight, followed by resin settling and aspiration of the supernatant fraction. The resin was then packed into a 2.6 cm diameter column and the column washed sequentially with PBS, pH 7.5 and 10 mM phosphate buffer, pH 8.0 at a flow rate of 5 ml/min. When absorbance at 280 nm reached a baseline level, bound material was eluted using 100 mM triethylamine and fractions under the single large peak of 280 nm absorbance were collected and tested for the presence of p68 by ELISA. Fractions containing p68 were pooled and dialyzed against PBS to remove triethylamine.

An experimental vaccine serial formulated was formulated to contain approximately 100 micrograms of purified p68 and 1% aluminum hydroxide gel. Formalin (0.01%) was used as a preservative in a final vaccine dose volume of 1 mL.

Challenge Inoculum

Challenge material was prepared essentially as described in examples above.

Study Procedure

Twenty-one (21) seronegative and culture negative pups were randomly assigned to one of two treatment groups. Eleven dogs were assigned to the non-vaccintated, control group and ten dogs to the vaccinated group. Day 0 was designated as the day of first vaccination. One mL of vaccine was administered subcutaneously on Day 0 and repeated 21 days later. Blood was collected for serological p68 ELISA prior to first and second vaccination.

On Day 35, fourteen days after the second vaccination, an aerosol challenge of B. bronchiseptica was administered to all dogs as described above. Animals were monitored for coughing for 14 days following challenge as described in previous examples.

Results
Summary of clinical observations and serologic responses to p68 are presented in Table 40.

TABLE 40

| | | Summary of Clinical Observations and Serologic Responses | | | |
|---|---|---|---|---|---|
| Group | N | Number COUGH ON TWO CONSECUTIVE DAYS | NORMAL/ TOTAL | TITER (gmt) PRE-vAX | TITER (gmt) PRE-CHALLENGE | TITER (gmt) POSTCHALLENGE |
| VACCINE | 10 | 0 | 10/10 | 5.08 | 348.15 | 391.30 |
| CONTROL | 11 | 11 | 0/11 | 6.10 | 6.45 | 18.81 |

Discussion

In this study, 10 of 10 control dogs coughed on at least two consecutive days. A dog is considered clinically diseased if it coughs for two consecutive days. By this criteria, 100% of the non-vaccinated control dogs were diseased. In the vaccinated group, one dog coughed on day 4 post-challenge and one dog coughed on days 4 and 6 post-challenge. Two dogs coughed on day 14. None of the vaccinated dogs coughed for two consecutive days. Therefore, 100% of the dogs in the native p68 vaccinated group were judged to remain normal following challenge.

Conclusions

This trial demonstrates the ability of a native p68 vaccine to protect against *B. bronchiseptica* disease.

What is claimed is:

1. A combination vaccine for immunizing a dog against canine pathogens comprising a preparation of a therapeutically effective amount of an attenuated strain of canine distemper (CD) virus, an attenuated strain of canine adenovirus type 2 (CAV-2), an attenuated strain of canine parainfluenza (CPI) virus and an attenuated strain of canine parvovirus (CPV); an inactivated whole or partial cell preparation of a strain of canine coronavirus (CCV), a *Bordetella bronchiseptica* p68 protein, and an adjuvant, wherein said *Bordetella bronchiseptica* p68 antigen comprises the amino acid sequence as set forth in SEQ ID NO: 1 and is produced recombinantly.

2. The combination vaccine of claim 1, wherein the amount of said attenuated strain of CD virus in said combination vaccine is in the range of $10^2$ to $10^9$ TCID$_{50}$ per dose.

3. The combination vaccine of claim 1, wherein the amount of said attenuated strain of CAV-2 in said combination vaccine is in the range of $10^2$ to $10^9$ TCID$_{50}$ per dose.

4. The combination vaccine of claim 1, wherein the amount of said attenuated strain of CPI virus in said combination vaccine is in the range of $10^2$ to $10^9$ TCID$_{50}$ per dose.

5. The combination vaccine of claim 1, wherein the amount of said attenuated strain of CPV in said combination vaccine is in the range of $10^2$ to $10^9$ TCID$_{50}$ per dose.

6. The combination vaccine of claim 1, wherein the amount of the cell preparation of said strain of CCV in said combination vaccine is at least about 100 relative units per dose.

7. The combination vaccine of claim 1, wherein said *Bordetella bronchiseptica* p68 antigen is produced recombinantly in *E. coli*.

8. The combination vaccine of claim 1, wherein the amount of said *Bordetella bronchiseptica* p68 protein is in the range of 0.5 μg to 1000 μg per dose.

9. The combination vaccine of claim 1 wherein said adjuvant comprises saponin and a surfactant.

10. The combination vaccine of claim 9, wherein said saponin is Quil A and said surfactant is cholesterol.

11. The combination vaccine of claim 10 wherein the amount of Quil A is in the range of 1 to 1000 μg per dose inclusive, and the amount of cholesterol is in the range of 1 to 1000 μg per dose.

* * * * *

```
                    SEQUENCE LISTING

<160> NUMBER OF SEQ ID NOS: 3

<210> SEQ ID NO 1
<211> LENGTH: 602
<212> TYPE: PRT
<213> ORGANISM: Bordetella bronchiseptica

<400> SEQUENCE: 1

Asp Pro Asn Thr Val Ser Ile Ile Lys Ala Gly Glu Arg Gln His Gly
1               5                   10                  15

Ile His Ile Lys Gln Ser Asp Gly Ala Gly Val Arg Thr Ala Thr Gly
            20                  25                  30

Thr Thr Ile Lys Val Ser Gly Arg Gln Ala Gln Gly Val Leu Leu Glu
        35                  40                  45

Asn Pro Ala Ala Glu Leu Arg Phe Gln Asn Gly Ser Val Thr Ser Ser
    50                  55                  60

Gly Gln Leu Phe Asp Glu Gly Val Arg Arg Phe Leu Gly Thr Val Thr
65                  70                  75                  80

Val Lys Ala Gly Lys Leu Val Ala Asp His Ala Thr Leu Ala Asn Val
                85                  90                  95

Ser Asp Thr Arg Asp Asp Asp Gly Ile Ala Leu Tyr Val Ala Gly Glu
            100                 105                 110

Gln Ala Gln Ala Ser Ile Ala Asp Ser Thr Leu Gln Gly Ala Gly Gly
        115                 120                 125

Val Arg Val Glu Arg Gly Ala Asn Val Thr Val Gln Arg Ser Thr Ile
    130                 135                 140

Val Asp Gly Gly Leu His Ile Gly Thr Leu Gln Pro Leu Gln Pro Glu
145                 150                 155                 160

Asp Leu Pro Pro Ser Arg Val Val Leu Gly Asp Thr Ser Val Thr Ala
                165                 170                 175

Val Pro Ala Ser Gly Ala Pro Ala Val Ser Val Phe Gly Ala Asn
            180                 185                 190
```

-continued

```
Glu Leu Thr Val Asp Gly Gly His Ile Thr Gly Gly Arg Ala Ala Gly
            195                 200                 205

Val Ala Ala Met Asp Gly Ala Ile Val His Leu Gln Arg Ala Thr Ile
        210                 215                 220

Arg Arg Gly Asp Ala Pro Ala Gly Gly Ala Val Pro Gly Gly Ala Val
225                 230                 235                 240

Pro Gly Gly Phe Gly Pro Leu Leu Asp Gly Trp Tyr Gly Val Asp Val
                245                 250                 255

Ser Asp Ser Thr Val Asp Leu Ala Gln Ser Ile Val Glu Ala Pro Gln
            260                 265                 270

Leu Gly Ala Ala Ile Arg Ala Gly Arg Gly Ala Arg Val Thr Val Ser
        275                 280                 285

Gly Gly Ser Leu Ser Ala Pro His Gly Asn Val Ile Glu Thr Gly Gly
    290                 295                 300

Gly Ala Arg Arg Phe Pro Pro Ala Ser Pro Leu Ser Ile Thr Leu
305                 310                 315                 320

Arg Ala Gly Ala Arg Ala Gln Gly Arg Ala Leu Leu Tyr Arg Val Leu
                325                 330                 335

Pro Glu Pro Val Lys Leu Thr Leu Ala Gly Gly Ala Gln Gly Gln Gly
            340                 345                 350

Asp Ile Val Ala Thr Glu Leu Pro Pro Ile Pro Gly Ala Ser Ser Gly
        355                 360                 365

Pro Leu Asp Val Ala Leu Ala Ser Gln Ala Arg Trp Thr Gly Ala Thr
    370                 375                 380

Arg Ala Val Asp Ser Leu Ser Ile Asp Asn Ala Thr Trp Val Met Thr
385                 390                 395                 400

Asp Asn Ser Asn Val Gly Ala Leu Arg Leu Ala Ser Asp Gly Ser Val
                405                 410                 415

Asp Phe Gln Gln Pro Ala Glu Ala Gly Arg Phe Lys Val Leu Met Val
            420                 425                 430

Asp Thr Leu Ala Gly Ser Gly Leu Phe Arg Met Asn Val Phe Ala Asp
        435                 440                 445

Leu Gly Leu Ser Asp Lys Leu Val Val Met Arg Asp Ala Ser Gly Gln
    450                 455                 460

His Arg Leu Trp Val Arg Asn Ser Gly Ser Glu Pro Ala Ser Ala Asn
465                 470                 475                 480

Thr Met Leu Leu Val Gln Thr Pro Arg Gly Ser Ala Ala Thr Phe Thr
                485                 490                 495

Leu Ala Asn Lys Asp Gly Lys Val Asp Ile Gly Thr Tyr Arg Tyr Arg
            500                 505                 510

Leu Ala Ala Asn Gly Asn Gly Gln Trp Ser Leu Val Gly Ala Lys Ala
        515                 520                 525

Pro Pro Ala Pro Lys Pro Ala Pro Gln Pro Gly Pro Gln Pro Gly Pro
    530                 535                 540

Gln Pro Gly Pro Gln Pro Gln Pro Gln Pro Gln Pro Gln Pro Gln Pro
545                 550                 555                 560

Gln Arg Gln Pro Glu Ala Pro Ala Pro Gln Pro Pro Ala Gly Arg Glu
                565                 570                 575

Leu Ser Ala Ala Ala Asn Ala Ala Val Asn Thr Gly Gly Val Gly Leu
            580                 585                 590

Ala Ser Thr Leu Trp Tyr Ala Glu Ser Asn
        595                 600
```

<210> SEQ ID NO 2
<211> LENGTH: 1806
<212> TYPE: DNA
<213> ORGANISM: Bordetella bronchiseptica

<400> SEQUENCE: 2

| | |
|---|---|
| gatccaaaca ctgtgtcaat catcaaggcc ggcgagcgcc agcacggcat ccacatcaag | 60 |
| caaagcgatg cgccggcgt acggaccgcc accggaacga ccatcaaggt aagcggtcgt | 120 |
| caggcccagg gcgtcctgct ggaaaatccc gcggccgagc tgcggttcca aacggcagc | 180 |
| gtcacgtctt cgggacagct gttcgacgaa ggcgtccggc gctttctggg caccgtcacc | 240 |
| gtcaaggccg gcaagctggt cgccgatcac gccacgctgg ccaacgtcag cgacacccgg | 300 |
| gacgacgacg catcgcgct ctatgtggcc ggcgagcagg cccaggccag catcgccgac | 360 |
| agcaccctgc agggcgcggg cggcgtgcgg gtcgagcgcg cgccaatgt cacggtccaa | 420 |
| cgcagcacca tcgttgacgg gggcttgcat atcggcaccc tgcagccgct gcagccggaa | 480 |
| gaccttccgc ccagccgggt ggtgctgggc gacaccagc tgaccgccgt gcccgccagc | 540 |
| ggcgcgcccg cggcggtgtc tgtattcggg gccaatgagc ttacggttga tggcgggcac | 600 |
| atcaccgggg ggcgggcagc gggggtggcg gccatggacg gggcgatcgt gcatctgcag | 660 |
| cgcgcgacga tacggcgggg ggacgcgcct gccggcggtg cggttccagg cggtgcggtt | 720 |
| cccggcggct tcggccccct ccttgacggc tggtatggcg tggatgtatc ggactccacc | 780 |
| gtggacctcg ctcagtcgat cgtcgaggcg ccgcagctgg gcgccgcgat ccgggcgggc | 840 |
| cgcggcgcca gggtgacggt gtcgggcggc agcttgtccg caccgcacgg caatgtcatc | 900 |
| gagaccggcg gcggtgcgcg tcgcttcccg cctccggcct cgccctgtc gatcaccttg | 960 |
| cgggcgggcg cacgggcgca ggggagggcg ctgctgtacc gggtcctgcc ggagcccgtg | 1020 |
| aagctgacgc tggcgggcgg cgcccagggg cagggcgaca tcgtcgcgac ggagctgcct | 1080 |
| cccattccag gcgcgtcgag cgggccgctc gacgtggcgc tggccagcca ggcccgatgg | 1140 |
| acgggcgcta cccgcgcggt cgactcgctg tccatcgaca acgccacctg ggtcatgacg | 1200 |
| gacaactcga acgtcggcgc gctgcggctg ccagcgacg cagcgtcga tttccagcag | 1260 |
| ccggccgaag ctgggcggtt caaggtcctg atggtcgata cgctggcggg ttcggggctg | 1320 |
| ttccgcatga atgtcttcgc ggacctgggg ctgagcgaca agctggtcgt catgcgggac | 1380 |
| gccagcggcc agcacaggct gtgggtccgc aacagcggca gcgagccggc cagcgccaac | 1440 |
| accatgctgc tggtgcagac gccacgagge agcgcggcga cctttaccct tgccaacaag | 1500 |
| gacggcaagg tcgatatcgg tacctaccgc tatcgattgg ccgccaacgg caatgggcag | 1560 |
| tggagcctgg tgggcgcgaa ggcgccgccg gcgcccaagc ccgcgccgca gcccggtccc | 1620 |
| cagcccggtc cccagcccgg tccccagccg ccgcagccgc cgcagccgcc gcagccgcca | 1680 |
| cagaggcagc cggaagcgcc ggcgccgcaa ccgccggcgg gcagggagtt gtccgccgcc | 1740 |
| gccaacgcgg cggtcaacac gggtgggggtg ggcctggcca gcacgctctg gtacgccgaa | 1800 |
| agcaat | 1806 |

<210> SEQ ID NO 3
<211> LENGTH: 599
<212> TYPE: PRT
<213> ORGANISM: Bordetella bronchiseptica

<400> SEQUENCE: 3

Asp Trp Asn Asn Gln Ser Ile Ile Lys Ala Gly Glu Arg Gln His Gly
1               5                   10                  15

-continued

```
Ile His Ile Lys Gln Ser Asp Gly Ala Gly Val Arg Thr Ala Thr Gly
             20                  25                  30

Thr Thr Ile Lys Val Ser Gly Arg Gln Ala Gln Gly Val Leu Leu Glu
         35                  40                  45

Asn Pro Ala Ala Glu Leu Arg Phe Gln Asn Gly Ser Val Thr Ser Ser
 50                  55                  60

Gly Gln Leu Phe Asp Glu Gly Val Arg Arg Phe Leu Gly Thr Val Thr
 65                  70                  75                  80

Val Lys Ala Gly Lys Leu Val Ala Asp His Ala Thr Leu Ala Asn Val
                 85                  90                  95

Ser Asp Thr Arg Asp Asp Gly Ile Ala Leu Tyr Val Ala Gly Glu
             100                 105                 110

Gln Ala Gln Ala Ser Ile Ala Asp Ser Thr Leu Gln Gly Ala Gly Gly
         115                 120                 125

Val Arg Val Glu Arg Gly Ala Asn Val Thr Val Gln Arg Ser Thr Ile
         130                 135                 140

Val Asp Gly Gly Leu His Ile Gly Thr Leu Gln Pro Leu Gln Pro Glu
145                 150                 155                 160

Asp Leu Pro Pro Ser Arg Val Val Leu Gly Asp Thr Ser Val Thr Ala
                 165                 170                 175

Val Pro Ala Ser Gly Ala Pro Ala Ala Val Ser Val Phe Gly Ala Asn
             180                 185                 190

Glu Leu Thr Val Asp Gly Gly His Ile Thr Gly Gly Arg Ala Ala Gly
             195                 200                 205

Val Ala Ala Met Asp Gly Ala Ile Val His Leu Gln Arg Ala Thr Ile
         210                 215                 220

Arg Arg Gly Asp Ala Pro Ala Gly Gly Ala Val Pro Gly Gly Ala Val
225                 230                 235                 240

Pro Gly Gly Phe Gly Pro Leu Leu Asp Gly Trp Tyr Gly Val Asp Val
                 245                 250                 255

Ser Asp Ser Thr Val Asp Leu Ala Gln Ser Ile Val Glu Ala Pro Gln
             260                 265                 270

Leu Gly Ala Ala Ile Arg Ala Gly Arg Gly Ala Arg Val Thr Val Ser
         275                 280                 285

Gly Gly Ser Leu Ser Ala Pro His Gly Asn Val Ile Glu Thr Gly Gly
         290                 295                 300

Gly Ala Arg Arg Phe Pro Pro Ala Ser Pro Leu Ser Ile Thr Leu
305                 310                 315                 320

Gln Ala Gly Ala Arg Ala Gln Gly Arg Ala Leu Leu Tyr Arg Val Leu
             325                 330                 335

Pro Glu Pro Val Lys Leu Thr Leu Ala Gly Gly Ala Gln Gly Gln Gly
             340                 345                 350

Asp Ile Val Ala Thr Glu Leu Pro Pro Ile Pro Gly Ala Ser Ser Gly
         355                 360                 365

Pro Leu Asp Val Ala Leu Ala Ser Gln Ala Arg Trp Thr Gly Ala Thr
 370                 375                 380

Arg Ala Val Asp Ser Leu Ser Ile Asp Asn Ala Thr Trp Val Met Thr
385                 390                 395                 400

Asp Asn Ser Asn Val Gly Ala Leu Arg Leu Ala Ser Asp Gly Ser Val
                 405                 410                 415

Asp Phe Gln Gln Pro Ala Glu Ala Gly Arg Phe Lys Cys Leu Met Val
             420                 425                 430
```

-continued

```
Asp Thr Leu Ala Gly Ser Gly Leu Phe Arg Met Asn Val Ala Phe Ala
        435                 440                 445

Asp Leu Gly Leu Ser Asp Lys Leu Val Val Met Arg Asp Ala Ser Gly
        450                 455                 460

Gln His Arg Leu Leu Val Arg Asn Ser Gly Ser Glu Pro Ala Ser Gly
465                 470                 475                 480

Asn Thr Met Leu Leu Val Gln Thr Pro Arg Gly Ser Ala Ala Thr Phe
                485                 490                 495

Thr Leu Ala Asn Lys Asp Gly Lys Val Asp Ile Gly Thr Tyr Arg Tyr
            500                 505                 510

Arg Leu Ala Ala Asn Gly Asn Gly Gln Trp Ser Leu Val Gly Ala Lys
            515                 520                 525

Ala Pro Pro Ala Pro Lys Pro Ala Pro Gln Pro Gly Pro Gln Pro Gly
        530                 535                 540

Pro Gln Pro Pro Gln Pro Pro Gln Pro Pro Gln Pro Pro Gln Arg Gln
545                 550                 555                 560

Pro Glu Ala Pro Ala Pro Gln Pro Pro Ala Gly Arg Glu Leu Ser Ala
                565                 570                 575

Ala Ala Asn Ala Ala Val Asn Thr Gly Gly Val Gly Leu Ala Ser Thr
            580                 585                 590

Leu Trp Tyr Ala Glu Ser Asn
        595
```